(12) United States Patent
Lahann et al.

(10) Patent No.: US 12,023,388 B2
(45) Date of Patent: *Jul. 2, 2024

(54) DETECTION AND TREATMENT OF CARIES AND MICROCAVITIES WITH NANOPARTICLES

(71) Applicants: THE REGENTS OF THE UNIVERSITY OF MICHIGAN, Ann Arbor, MI (US); POZNAN UNIVERSITY OF MEDICAL SCIENCES, Poznan (PL)

(72) Inventors: Joerg Lahann, Ann Arbor, MI (US); Sywe-Ren Chang, Ann Arbor, MI (US); Brian Clarkson, Ann Arbor, MI (US); Nathan A. Jones, Ann Arbor, MI (US); Agata Czajka-Jakubowska, Poznan (PL)

(73) Assignees: The Regents of The University of Michigan, Ann Arbor, MI (US); POZNAN UNIVERSITY OF MEDICAL SCIENCES, Poznan (PL)

(*) Notice: Subject to any disclaimer, the term of this patent is extended or adjusted under 35 U.S.C. 154(b) by 0 days.

This patent is subject to a terminal disclaimer.

(21) Appl. No.: 17/228,039

(22) Filed: Apr. 12, 2021

(65) Prior Publication Data

US 2021/0228744 A1 Jul. 29, 2021

Related U.S. Application Data

(63) Continuation of application No. 15/331,408, filed on Oct. 21, 2016, now Pat. No. 10,987,434.

(60) Provisional application No. 62/244,512, filed on Oct. 21, 2015.

(51) Int. Cl.
| | |
|---|---|
| A61K 49/00 | (2006.01) |
| A61K 8/02 | (2006.01) |
| A61K 8/21 | (2006.01) |
| A61K 8/24 | (2006.01) |
| A61K 8/25 | (2006.01) |
| A61K 8/55 | (2006.01) |
| A61K 8/64 | (2006.01) |
| A61K 8/72 | (2006.01) |
| A61K 8/73 | (2006.01) |
| A61Q 11/00 | (2006.01) |

(52) U.S. Cl.
CPC ........ *A61K 49/0054* (2013.01); *A61K 8/0241* (2013.01); *A61K 8/21* (2013.01); *A61K 8/24* (2013.01); *A61K 8/25* (2013.01); *A61K 8/55* (2013.01); *A61K 8/64* (2013.01); *A61K 8/72* (2013.01); *A61K 8/732* (2013.01); *A61K 8/736* (2013.01); *A61K 49/0043* (2013.01); *A61K 49/0093* (2013.01); *A61Q 11/00* (2013.01); *A61K 2800/413* (2013.01); *A61K 2800/42* (2013.01); *A61K 2800/434* (2013.01); *A61K 2800/5426* (2013.01); *A61K 2800/57* (2013.01); *A61K 2800/654* (2013.01); *A61K 2800/81* (2013.01); *A61K 2800/92* (2013.01)

(58) Field of Classification Search
CPC .... A61K 49/0054; A61K 8/0241; A61K 8/21; A61K 8/24; A61K 8/25; A61K 8/55; A61K 8/64; A61K 8/72; A61K 2800/81; A61K 2800/92; A61Q 11/00
See application file for complete search history.

(56) References Cited

U.S. PATENT DOCUMENTS

| | | | |
|---|---|---|---|
| 5,063,046 A | * | 11/1991 | Grollier ................ A61Q 11/00 424/78.08 |
| 5,801,226 A | | 9/1998 | Cummins et al. |
| 6,428,814 B1 | | 8/2002 | Bosch et al. |
| 6,589,562 B1 | | 7/2003 | Shefer et al. |
| 6,677,386 B1 | | 1/2004 | Giezen et al. |

(Continued)

FOREIGN PATENT DOCUMENTS

| | | | | |
|---|---|---|---|---|
| AU | 2011202746 A1 | * | 6/2011 | ............... A23G 3/36 |
| CN | 101287674 A | | 10/2008 | |

(Continued)

OTHER PUBLICATIONS

Partial European Search Report regarding Patent Application No. 221830870, dated Aug. 9, 2022.

(Continued)

*Primary Examiner* — Robert S Cabral
(74) *Attorney, Agent, or Firm* — Harness, Dickey & Pierce, P.L.C.

(57) ABSTRACT

Components, for example, nanoparticles for detecting and/or treating one or more active carious lesions or microcavities in teeth of a subject are provided. The component or nanoparticle may comprise a biocompatible and biodegradable polymer (e.g., a starch) bearing at least one cationic region and/or having a net positive charge and thereby capable of associating with one or more active and/or early carious lesions on a tooth in an oral cavity of a subject. The components or nanoparticles are optionally water soluble or dispersible. The components or nanoparticle also comprises an imaging agent (e.g., a fluorophore or dye) bonded to the biocompatible and biodegradable polymer. The component or nanoparticle is thus capable of indicating the presence of one or more active carious lesions when the component or nanoparticle is associated therewith. Oral care compositions comprising such compounds/nanoparticles and methods of making and using the same are also provided.

19 Claims, 15 Drawing Sheets

(56) References Cited

U.S. PATENT DOCUMENTS

| | | |
|---|---|---|
| 6,755,915 B1 | 6/2004 | Van Soest et al. |
| 7,767,017 B2 | 8/2010 | Lahann et al. |
| 7,947,772 B2 | 5/2011 | Lahann et al. |
| 8,043,480 B2 | 10/2011 | Lahann et al. |
| 8,048,404 B1 | 11/2011 | Sung et al. |
| 8,052,849 B2 | 11/2011 | Lahann et al. |
| 8,187,708 B2 | 5/2012 | Lahann et al. |
| 9,566,247 B2 | 2/2017 | Koo et al. |
| 10,285,943 B2 | 5/2019 | Bloembergen et al. |
| 2002/0119100 A1 | 8/2002 | Okada et al. |
| 2005/0191359 A1 | 9/2005 | Goldshtein et al. |
| 2007/0086964 A1 | 4/2007 | Moran et al. |
| 2007/0237800 A1 | 10/2007 | Lahann |
| 2008/0038686 A1 | 2/2008 | Nagai |
| 2008/0170764 A1 | 7/2008 | Burns et al. |
| 2010/0092548 A1 | 4/2010 | Xie et al. |
| 2010/0204448 A1 | 8/2010 | Szeto et al. |
| 2010/0272639 A1 | 10/2010 | Dutcher |
| 2011/0042841 A1 | 2/2011 | Wildi et al. |
| 2011/0110575 A1 | 5/2011 | Banumathi et al. |
| 2012/0045487 A1 | 2/2012 | Lahann et al. |
| 2012/0141551 A1 | 6/2012 | Bloembergen et al. |
| 2012/0189543 A1 | 7/2012 | Wang et al. |
| 2012/0269729 A1 | 10/2012 | Santra et al. |
| 2013/0039848 A1 | 2/2013 | Bradbury et al. |
| 2013/0115169 A1 | 5/2013 | Lahann et al. |
| 2014/0147510 A1 | 5/2014 | Lahann et al. |
| 2014/0161745 A1 | 6/2014 | Almhojd et al. |
| 2014/0182797 A1 | 7/2014 | Paltakari et al. |
| 2015/0152197 A1 | 6/2015 | Akhlaghi et al. |

FOREIGN PATENT DOCUMENTS

| | | | |
|---|---|---|---|
| CN | 101426448 A | 5/2009 | |
| CN | 101501107 A | 8/2009 | |
| CN | 102112100 A | 6/2011 | |
| CN | 103421195 A | 12/2013 | |
| CN | 103501821 A | 1/2014 | |
| CN | 104069013 A | 10/2014 | |
| CN | 104507458 A | 4/2015 | |
| EP | 0736544 A1 | 10/1996 | |
| EP | 1176254 A1 | 1/2002 | |
| GB | 1420392 A | 1/1976 | |
| JP | H1017446 A | 1/1998 | |
| JP | H10511957 A | 11/1998 | |
| JP | 2000063290 A | 2/2000 | |
| JP | 2003511406 A | 3/2003 | |
| JP | 2009534097 A | 9/2009 | |
| JP | 2014505672 A | 3/2014 | |
| JP | 2018536021 A | 12/2018 | |
| JP | 2022051758 A | 4/2022 | |
| WO | 9620698 A2 | 7/1996 | |
| WO | 0208516 A1 | 1/2002 | |
| WO | 06137936 A2 | 12/2006 | |
| WO | 2007123880 A2 | 11/2007 | |
| WO | 2007149310 A2 | 12/2007 | |
| WO | 2009055693 A2 | 4/2009 | |
| WO | 2009151421 A1 | 12/2009 | |
| WO | 2010011641 A2 | 1/2010 | |
| WO | WO-2010012473 A2 | 2/2010 | |
| WO | 2010065750 A1 | 6/2010 | |
| WO | 2010084088 A2 | 7/2010 | |
| WO | 2010127119 A2 | 11/2010 | |
| WO | 2011071742 A2 | 6/2011 | |
| WO | WO-2011128931 A1 | 10/2011 | |
| WO | 2011003109 A8 | 2/2012 | |
| WO | 2013081720 A1 | 6/2013 | |
| WO | WO-2013081720 A1 * | 6/2013 | ........... A61K 31/704 |
| WO | 2014130994 A1 | 8/2014 | |
| WO | 2015144991 A1 | 10/2015 | |
| WO | WO-2015183995 A2 | 12/2015 | |

OTHER PUBLICATIONS

Japanese Office Action regarding Application No. 2022-004069 dated Mar. 31, 2023.

Benjamin Horev et al.; "pH-Activated Nanoparticles for Controlled Topical Delivery of Farnesol to Disrupt Oral Biofilm Virulence"; American Chemical Society, 2015, 9, 3, 2390-2404; Feb. 9, 2015; https://doi.org/10.1021/nn507170s; 5 pages.

Examiner Requisition for Canadian Application No. 3,039,906 dated Jan. 23, 2023; 6 pages.

Araujo Cintia T. P. et al.; "Influence of Fluorescent Dye on Mechanical Properties of Adhesive Systems"; International Journal of Adhesion and Adhesives, Elsevier, Amsterdam, NL, vol. 47, Aug. 30, 2013; pp. 129-133, xp028771096, ISSN: 0143-7496, DOI: 10.1016/J.IJADHADH.2013.08.007.

European Search Report for EP Application No. 22183087.0 dated Oct. 18, 2022; 23 pages.

Anonymous, "Featuring Photoacoustic Imaging, Nanosafety and More: January's Advanced Healthcare Materials Covers," Advanced Science News (Jan. 31, 2017) [online] [Retrieved from the internet on Aug. 6, 2020] URL: <https://www.advancedsciencenews.com/featuring-photoacoustic-imaging-nanosafety-januarys-advanced-healthcare-materials-covers/>, 3 pages.

Anonymous, "Nanoparticles release drugs to reduce tooth decay," Phys. Org (Apr. 1, 2015) [online] [Retrieved from the internet Aug. 3, 2020] URL: <https://phys.org/news/2015-04-nanoparticles-drugs-tooth.html>, 2 pages.

B. Clarkson, et al., "Redistribution of enamel fluoride during white spot lesion formation: an in vitro study on human dental enamel." Caries Res. 1981, 15.

Bader, J.D., et al. "Diagnosis and management of dental caries: summary." AHRQ Evidence Report Summaries, 2001.

First Office Action for Brazilian Patent Application No. BR112018007986-3 dated May 26, 2020 with English language translation, 8 pages.

First Office Action for Chinese Patent Application No. 201680075282.9 dated Aug. 3, 2020 with English language translation, 24 pages.

First Office Action for European Patent Application No. 16858371.4 dated Oct. 5, 2020, 5 pages.

First Office Action for Japanese Patent Application No. 2018-540696 dated Oct. 20, 2020, with English language translation, 12 pages.

Fischer, Kathrin, Scientific Documentation: Plaque Test, Ivoclar Vivadent® (Aug. 2012), 12 pages [retrieved from the Internet] [retrieved on Aug. 6, 2020] URL: <https://www.ivoclarvivadent.com/en/p/all/products/prevention-care/caries-isk/plaque-test>.

Huanga Y. et al. "Ultra-small and innocuous cationic starch nanospheres: Preparation, characterization and drug delivery study." International Journal of Biological Macromolecules, 58: pp. 231-239 (2013).

International Search Report regarding Application No. PCT/US2016/058274, dated Jan. 11, 2017.

Jones, Nathan A., "Harnessing Functionalized Polysaccharides for Medical and Dental Applications," Doctoral Dissertation, University of Michigan, Horace H. Rackham School of Graduate Studies (2017) (Published Jan. 31, 2018), 132 pages.

Jones, Nathan A., et al., "Nanoparticle-Based Targeting and Detection of Microcavities," Advanced Healthcare Materials, 6(1), 1600883; (Published Nov. 15, 2016) DOI: 10.1002/adhm.201600883.

Kato, Y. et al., "Oxidation process of water-soluble starch in TEMPO-mediated system," Carbohydrate Polymers 51, pp. 69-75 (2003).

Lippert et al. "Dentifrice fluoride and abrasivity interplay on artificial caries lesions" Caries Research 46 pp. 23-30, 2014.

Lippert et al. "Effect of Fluoride, Lesion Baseline Severity and Mineral Distribution on Lesion Progression" Caries Research 46 pp. 23-30 (2012).

Misra, A.C., Bhaskar, S., Clay, N., Lahann, J., "Multicompartmental Particles for Combined Imaging and siRNA Delivery", Advanced Materials, 2012.

Nascimento, Marcelle and Xiao, Jin—International Association for Dental Research. Letter to Nathan Jones. Mar. 4, 2016, 1 page.

NIH NIDCR data—http://www.nidcr.nih.gov/DataStatistics/. Accessed on Dec. 29, 2016.

(56) References Cited

OTHER PUBLICATIONS

Partial Supplementary European Search Report for European Patent Application No. 16858371.4 dated Feb. 21, 2019, 15 pages.
Parveen, S., Misra, R. Sahoo, S., "Nanoparticles: a boon to drug delivery, therapeutics, diagnostics, and imaging." Nanomedicine: Nanotechnology, Biology, and Medicine, 8:2, pp. 147-166, 2012.
Roh et al., "Biphasic Janus Particles With Nanoscale Anisotropy", Nature Materials, vol. 4, pp. 759-763 (Oct. 2005).
Second Office Action for Chinese Patent Application No. 201680075282.9 dated Mar. 17, 2021 with English language translation, 20 pages.
Shuman, Lou, "Focus On: Disruptive Technologies for 2020," Dentistry Today (Mar. 27, 2020) [online] [Retrieved from the internet: Aug. 5, 2020] URL: <https://www.dentistrytoday.com/focus-on/10675-focus-on-disruptive-technologies-for-2020>, 2 pages.
Song, Delong, Yonathan S. Thio, and Yulin Deng. "Starch Nanoparticle Formation Via Reactive Extrusion and Related Mechanism Study." Carbohydrate Polymers, vol. 85, No. 1, 2011., pp. 208-214doi:10.1016/j.carbpol.2011.02.016.
Supplementary European Search Report for European Patent Application No. 16858371.4 dated Jun. 19, 2019, 14 pages.
Vasir, J., Labhasetwar, V. "Targeted drug delivery in cancer therapy." Technol Cancer Res Treat. 4:4, pp. 363-374, 2005.
Website, Nanoparticles release drugs to reduce tooth decay, Apr. 1, 2015 (URL: http://phys.org/news/2015-04-nanoparticles-drugs-tooth.html). Accessed on Jan. 19, 2017.
Weerkamp, A. H. et al., "Effect of Zeta Potential and Surface Energy on Bacterial Adhesion to Uncoated and Saliza-coated Human Enamel and Dentin," J. Dent. Res. 67(12), pp. 1483-1487 (Dec. 1988).

Written Opinion of International Searching Authority regarding Application No. PCT/US2016/058274, dated Jan. 11, 2017.
Young, A. et al., "Zeta Potentials of Human Enamel and Hydroxyapatite as Measured by the Coulter® DELSA 440," Adv. Dent. Res. 1194), pp. 560-565 (Nov. 1997).
First Office Action for Chinese Application No. 202111237630.7 dated Mar. 31, 2023.
Second Office Action for Chinese Application No. 202111237630.7 dated Nov. 30, 2023; 12 pages.
Second Office Action for Canadian Application No. 3,039,906 dated Oct. 11, 2023; 8 pages.
Second Office Action for Japanese Application No. 2018-540696, dated Sep. 12, 2023.
Bennett Tochukwu Amaechi et al.; "Evaluation of a novel caries detecting oral rinse"; BDJ Open; Springer Nature; published online Mar. 20, 2023; 8 pages.
Nathan A. Jones et al.; "Early occlusal caries detection using targeted fluorescent starch nanoparticles"; Journal of Dentistry, 125; available online Jul. 27, 2022; 6 pages.
First Office Action for Korean Patent Application No. 1020187014314, issued Mar. 19, 2024.
Japanese Final Office Action regarding Patent Application No. 2022004069, dated Dec. 26, 2023.
First Office Action/Search Report for Brazilian Patent Application No. 1220190219303, issued Apr. 9, 2024.
Oliveira, Dayane et al.; "Influence of Fluorescent Dye on Physical-Mechanical Properties of Luting Cements for Confocal Microscopy Analysis"; Microscopy Research & Technique; Dec. 2014; 77(12):986-8; https://doi.org/10.1002/jemt.22426.

\* cited by examiner

A

| StNP Sample | Zeta Potential (mV) | DLS Size (nm) (intensity-weighted) | NTA Size (nm) (number-weighted) |
|---|---|---|---|
| Unmodified (1) | -0.6 ± 1.0 | 53 ± 23 | 41 ± 28 |
| Cationic (2) | +22.7 ± 1.3 | 35 ± 33 | 20 ± 11 |
| Anionic (5) | -30.5 ± 3.0 | 90 ± 76 | 24 ± 17 |
| Zwitterionic (3) | +8.2 ± 2.0 | 250 ± 110 | 101 ± 33 |
| Anionic Fluorescein (6) | -9.3 ± 2.3 | 36 ± 32 | 45 ± 33 |
| Cationic Fluorescein (4) | +5.8 ± 1.2 | 209 ± 110 | 101 ± 56 |

B

| Sample | Initial Iodine [red intensity/10] | Final Iodine [red intensity/10] | Initial Benedict's Adsorption @ 575 nm | Final Benedict's Adsorption @ 575 nm |
|---|---|---|---|---|
| 1 | 11.0 ± 0.03 | 0.5 ± 0.001 | 0.22 ± 0.01 | 1.34 ± 0.17 |
| 3 | 2.5 ± 0.01 | 1.5 ± 0.02 | 0.13 ± 0.01 | 0.56 ± 0.03 |
| 4 | 3.5 ± 0.03 | 2.2 ± 0.005 | 0.26 ± 0.01 | 0.68 ± 0.09 |

Figures 3A–3B

DETECTION AND TREATMENT OF CARIES AND MICROCAVITIES WITH NANOPARTICLES

CROSS-REFERENCE TO RELATED APPLICATIONS

This application is a continuation of U.S. patent application Ser. No. 15/331,408 filed Oct. 21, 2016 which will issue as U.S. Pat. No. 10,987,434 on Apr. 27, 2021, which claims the benefit of U.S. Provisional Application No. 62/244,512, filed on Oct. 21, 2015. The entire disclosures of the above applications are incorporated herein by reference.

FIELD

The present disclosure relates to nanoparticles having diagnostic agents that can be delivered to an oral cavity of a subject to provide detection of caries and/or provide therapeutic treatment of caries, especially active (progressing) carious lesions.

BACKGROUND

This section provides background information related to the present disclosure which is not necessarily prior art.

Dental caries is the most common disease in dental health worldwide. In the United States, more than 90% of adults have experienced dental caries in their permanent teeth. Approximately 36% of the world's population has active caries. Furthermore, with developing countries gaining access to high sugar diets, the incidence of dental caries is likely to increase.

Dental cavities form when bacteria in the dental biofilm on the surface of teeth ferment sugars and produce acids which demineralize dentin and/or enamel. Early decalcification is indicated by white spot lesions forming on the surface enamel. These lesions, also called "microcavities" or incipient carious lesions, are reversible by a process called remineralizaton, which uses calcium and phosphorous in the saliva and is aided by the presence of fluoride in drinking water and toothpaste. However, if decalcification continues, irreversible cavitation occurs requiring a dental procedure to stop the decalcification.

Early forming caries are still reversible with improved oral hygiene, but are difficult to diagnose, and tactile methods can potentially cause permanent damage to teeth. For example, early stage caries (a white spot lesion) is reversible with improved oral hygiene and fluoride application; however demineralization weakens the tooth, leading to cavitation, which requires dental restoration. Thus, diagnosing and treating early carious lesions can reduce the need for more involved and expensive dental treatments. However, diagnosis of white spot lesions is challenging, as presentation is highly variable.

Primarily, caries diagnosis is carried out optically and tactically with a dental mirror and explorer, but optical detection can be difficult and tactile probing of carious lesions may accelerate cavitation. X-ray images of the teeth are routinely taken to identify cavities, particularly for regions in between teeth (interproximal caries). This method can clearly identify advanced cavity progression for dental treatment, but suffers from several limitations. First, X-ray images are unable to identify early forming lesions, which can still be repaired by an improved oral hygiene regimen and application of an active ingredient (e.g., fluoride application). Furthermore, X-rays are expensive for both the dentist and the patient. Additionally, radiation exposure from X-rays has been linked to cancer risk, thus providing an impetus to minimize the need for radiation based diagnostics.

A variety of new methods for caries diagnosis have been developed, but these require additional equipment, are expensive, and generally fail to distinguish between active (progressing) and inactive (not progressing) lesions. It would be desirable to have a method of detecting oral caries, especially early caries, which is easily administered and assessed, is biocompatible and has low toxicity, can dissolve or disintegrate in vivo at predetermined time intervals, and/or does not require extensive training or equipment for administration and/or detection.

SUMMARY

This section provides a general summary of the disclosure, and is not a comprehensive disclosure of its full scope or all of its features.

In certain aspects, the present disclosure contemplates a composition for oral administration. The composition may comprise a component or nanoparticle. The component or nanoparticle comprises an imaging agent, an active ingredient (e.g., a therapeutic agent), or combinations thereof. The composition has a cationic moiety or a net positive charge. The composition is thus capable of indicating the presence of one or more carious lesions when the component or nanoparticle is associated therewith. The component or nanoparticle may comprise a biocompatible, bio-based, and/or biodegradable polymer. In certain aspects, the biocompatible, bio-based, and/or biodegradable polymer may bear at least one cationic region or having a net positive charge that is capable of associating with one or more caries or carious lesions on a tooth in an oral cavity of a subject. In other aspects, an imaging agent may be optionally bonded to the biocompatible, bio-based and/or biodegradable polymer. In other aspects, the component or nanoparticle is capable of treating one or more carious lesions when the component or nanoparticle is associated therewith. In certain other aspects, the component or nanoparticle is capable of indicating the presence of one or more carious lesions and treating the one or more carious lesions when the component or nanoparticle is associated therewith. The oral care composition optionally further comprises an orally acceptable carrier.

In other aspects, the present disclosure contemplates a composition for oral administration. The composition may comprise a nanoparticle. The nanoparticle may comprise a biocompatible and biodegradable polymer. The biocompatible and biodegradable polymer optionally bears at least one cationic region capable of associating with one or more caries or carious lesions on a tooth in an oral cavity of a subject. In other aspects, the biocompatible and biodegradable polymer bears a net positive charge. The nanoparticle also comprises an imaging agent associated with (e.g., bonded to) the biocompatible and biodegradable polymer. The nanoparticle is thus capable of indicating the presence of one or more carious lesions when the nanoparticle is associated therewith.

In other variations, the present disclosure contemplates an oral care composition for oral administration in an oral cavity of a subject. The oral care composition may comprise a plurality of nanoparticles. Each nanoparticle may comprise a biocompatible and biodegradable polymer bearing at least one cationic region having a positive charge capable of associating with one or more caries or carious lesions on a tooth in the oral cavity of the subject. The oral care composition may also comprise an imaging agent bonded to the biocompatible and biodegradable polymer. The plurality of nanoparticles is capable of indicating the presence of one or more carious lesions when the nanoparticles are associated therewith. The oral care composition further comprises an orally acceptable carrier.

In certain other variations, methods of making a nanoparticle for oral administration are contemplated by the present disclosure. In one aspect, a method may comprise functionalizing a biocompatible and biodegradable polymer with a reactive group capable of reacting with an imaging agent. The biocompatible and biodegradable polymer comprises at least one cationic region capable of associating with one or more carious lesion on a tooth in an oral cavity of a subject. The method may thus further include reacting the reactive group on the biocompatible and biodegradable polymer with the imaging agent, so that the nanoparticle bears the imaging agent that is capable of indicating the presence of one or more carious lesions when the nanoparticle is associated therewith.

In other variations, a method of making a composition for oral administration is provided that comprises functionalizing a polymer with a reactive group capable of reacting with an imaging agent, wherein the polymer comprises at least one cationic region. The method further comprises reacting the reactive group on the polymer with the imaging agent, wherein the composition has a net positive charge.

The present disclosure further provides a method of detecting caries in yet other variations. The method comprises introducing a positively-charged fluorescent component to an oral cavity of a subject. Light is directed into the oral cavity and then identifying any fluorescence in the oral cavity that corresponds to a location of one or more caries in the oral cavity.

In other aspects, the present disclosure provides a method of treating caries comprising introducing a positively-charged nanoparticle comprising a remineralizing agent to an oral cavity of a subject, wherein the positively-charged nanoparticle is capable of associating with one or more carious lesions in the oral cavity of the subject.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 shows a graphical representation of a chemical reaction scheme for preparation of starch nanoparticles according to certain variations of the present disclosure. Unmodified nanoparticles (1) undergo cationization to prepare cationic particles (2). TEMPO oxidation on cationic particles (2) and unmodified particles (1) yields zwitterionic particles (3) and anionic particles (5), respectively. EDC/NHS chemistry is performed on particles (3) and (5) with fluorescein amine to yield fluorescently labeled cationic (4) and fluorescently labeled anionic (6) particles.

FIG. 2 shows FTIR spectra for unmodified (1), cationic (2), anionic (5), and zwitterionic (3) starch nanoparticles as described in the context of FIG. 1 above. Regions of interest for C—H and C=O peaks are highlighted.

FIGS. 3A-3B. FIG. 3A shows a chart that summarizes particle size and zeta potential results for modified starch nanoparticles (StNPs). Size is measured by intensity-weighted dynamic light scattering and number-weighted nanoparticle tracking analysis. FIG. 3B shows a chart summarizing starch degradation results for unmodified (1), zwitterionic (3), and fluorescent cationic (4) starch nanoparticles. The iodine column is a measure of red intensity, which decreases from initial to final states when exposed to saliva, indicating degradation of starch. The Benedict's reaction is measured by comparing absorption values at 575 nm and shows an increase in absorption after degradation by saliva, indicating the presence of reducing sugars. ($p<0.005$ for all final vs. initial comparisons).

FIGS. 4A-4B show starch degradation results for StNP-1 (unmodified), StNP-3 (zwitterionic), and StNP-4 (fluorescent cationic) starch nanoparticles. FIG. 4A shows levels of starch-iodine complex. FIG. 4B shows reducing sugars content by Benedict's test. Both graphs show initial levels and a final measurement after 30 minutes of exposure to salivary amylase in human saliva. The Benedict's reaction is measured by comparing absorption values at 575 nm and shows an increase in absorption after degradation by saliva, indicating the presence of reducing sugars. Results show that in the presence of saliva, starch and modified starch nanoparticles are degraded into simple sugars. ($p<0.005$ for all initial versus final comparisons).

FIGS. 5A-5B show fluorescence over time based on three washing conditions. FIG. 5A shows fluorescence over 2 hours (120 minutes). FIG. 5B shows fluorescence over 20 minutes.

FIG. 6 shows Tox8 cellular toxicity assay of modified StNPs after 2 hour exposure on HeLa cells. Even at high concentrations (1% by mass), all particles are non-toxic.

FIGS. 7A-7B. FIGS. 7A-7B show photographs of the same tooth before and after exposure to a plurality of cationic starch nanoparticles conjugated with an imaging agent prepared in accordance with certain aspects of the present disclosure. FIG. 7A is photograph of a tooth with artificially induced carious lesions without exposure to the fluorescent cationic starch nanoparticles, which does not illuminate any microcavities, while FIG. 7B is a photograph of the same tooth after exposure to the fluorescent cationic starch nanoparticles. FIG. 7B shows visible changes in the color of the tooth after exposure to the cationic starch nanoparticles conjugated with the imaging agent, when illuminated using a standard dental curing lamp.

FIG. 8 illustrates a bar graph showing a percent intensity difference of carious lesion intensity minus background tooth intensity, with corresponding illuminating images of tooth lesions above each control, and underneath the fluorescent cationic StNP bar (using a standard dental curing lamp). Statistical marks as follows: *Darker than background ($0.05<p<0.20$); †Significantly darker than background ($p<0.05$); ‡Significantly brighter than background ($p<10^{-5}$).

FIGS. 9A-9F. FIGS. 9A-9F illustrate a representative top-view 2-photon z-stack of images of a surface of carious lesions with respective dyes. The undyed blank tooth in FIG. 9A appears similar to the fluorescent FITC-dextran (FIG. 9B), fluorescein (FIG. 9C), fluorescent anionic StNP (FIG. 9D), and fluorescent cationic non-lesion (FIG. 9F) controls. The sample having carious lesions treated with fluorescent cationic StNPs (FIG. 9E) has a bright speckled appearance, with illuminated spots clearly identifying the lesions on the order of 5-10 microns in diameter and with depths of 5-15 microns.

FIG. 10 illustrates an example of cavity pore architecture illuminated by fluorescent cationic StNPs for detecting the presence of carious lesions according to certain aspects of the present disclosure. Nanoparticles prepared in accordance with certain aspects of the present disclosure adsorb to the lumen surface of the pore leaving a central gap. The carious lesion in this tooth is approximately 10 microns wide, by 8 microns deep.

FIGS. 11A-11B. FIG. 11A shows a graphical representation of X-ray Photon Spectroscopy (XPS) results for modified StNPs, indicating the presence of nitrogen on the order of 2% for cationic and zwitterionic StNPs. This corresponds to a theoretical reaction efficiency of 30-40% of glucose units. Additionally, presence of sodium and chloride is tracked as the most significant contaminant. FIG. 11B shows H'-NMR results for TEMPO oxidation as a function of sodium hypochlorite added. The peak shift corresponding to the C6 hydrogen from 5.2 to 5.4 ppm indicates conversion from hydroxyl to carboxyl on the order of 40-50% of glucose units.

Figure 15:
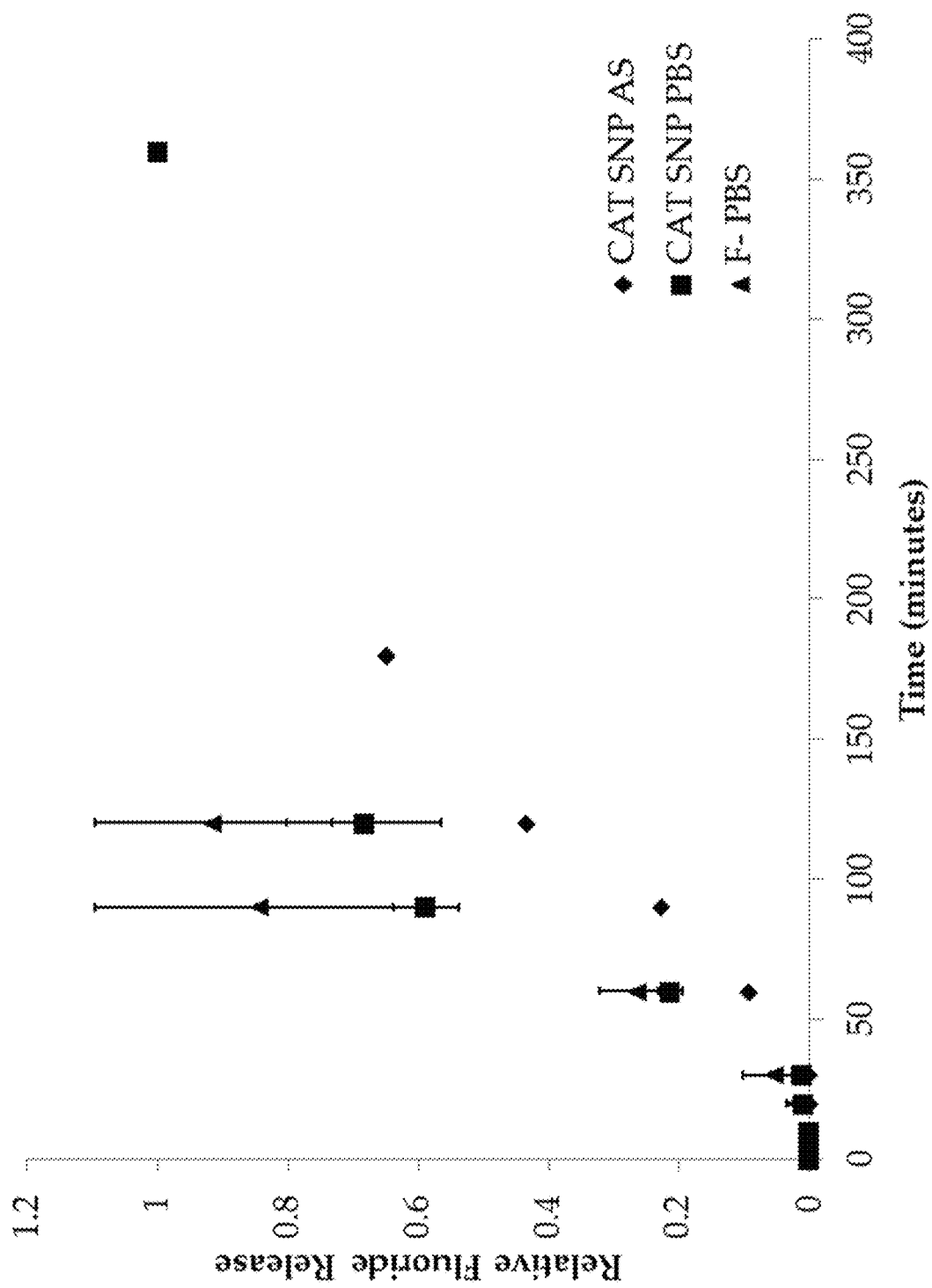

FIG. 15 shows results of a fluoride release study. The study indicates that there is slight delay on fluoride release when lyophilized with the cationic starch nanoparticles, on the order of about 30 minutes improvement in artificial saliva (AS) solution, or 10 minutes in phosphate-buffered-saline (PBS) solution. This preliminary data suggests that the cationic starch can moderately bind the anionic fluoride salt to extend release, with the implication that larger particles with cross-linking are needed to further extend the release profile.

DETAILED DESCRIPTION

Example embodiments are provided so that this disclosure will be thorough, and will fully convey the scope to those who are skilled in the art. Numerous specific details are set forth such as examples of specific compositions, components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, elements, compositions, steps, integers, operations, and/or components, but do not preclude the presence or addition of one or more other features, integers, steps, operations, elements, components, and/or groups thereof. Although the open-ended term "comprising," is to be understood as a non-restrictive term used to describe and claim various embodiments set forth herein, in certain aspects, the term may alternatively be understood to instead be a more limiting and restrictive term, such as "consisting of" or "consisting essentially of." Thus, for any given embodiment reciting compositions, materials, components, elements, features, integers, operations, and/or process steps, the present disclosure also specifically includes embodiments consisting of, or consisting essentially of, such recited compositions, materials, components, elements, features, integers, operations, and/or process steps. In the case of "consisting of," the alternative embodiment excludes any additional compositions, materials, components, elements, features, integers, operations, and/or process steps, while in the case of "consisting essentially of," any additional compositions, materials, components, elements, features, integers, operations, and/or process steps that materially affect the basic and novel characteristics are excluded from such an embodiment, but any compositions, materials, components, elements, features, integers, operations, and/or process steps that do not materially affect the basic and novel characteristics can be included in the embodiment.

Any method steps, processes, and operations described herein are not to be construed as necessarily requiring their performance in the particular order discussed or illustrated, unless specifically identified as an order of performance. It is also to be understood that additional or alternative steps may be employed, unless otherwise indicated.

When a component, element, or layer is referred to as being "on," "engaged to," "connected to," or "coupled to" another element or layer, it may be directly on, engaged, connected or coupled to the other component, element, or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various steps, elements, components, regions, layers and/or sections, these steps, elements, components, regions, layers and/or sections should not be limited by these terms, unless otherwise indicated. These terms may be only used to distinguish one step, element, component, region, layer or section from another step, element, component, region, layer or section. Terms such as "first," "second," and other numerical terms when used herein do not imply a sequence or order unless clearly indicated by the context. Thus, a first step, element, component, region, layer or section discussed below could be termed a second step, element, component, region, layer or section without departing from the teachings of the example embodiments.

Spatially or temporally relative terms, such as "before," "after," "inner," "outer," "beneath," "below," "lower,"

"above," "upper," and the like, may be used herein for ease of description to describe one element or feature's relationship to another element(s) or feature(s) as illustrated in the figures. Spatially or temporally relative terms may be intended to encompass different orientations of the device or system in use or operation in addition to the orientation depicted in the figures.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters.

In addition, disclosure of ranges includes disclosure of all values and further divided ranges within the entire range, including endpoints and sub-ranges given for the ranges.

The disclosure of all patents, patent applications, articles, and other publications referenced or cited in this disclosure are hereby incorporated by reference herein.

Example embodiments will now be described more fully with reference to the accompanying drawings.

Worldwide caries is the most common chronic disease and nearly all people will develop caries at some point in their lifetime. In the United States, national dental expenditure was estimated to be about $133.5 Billion in 2014, and is projected to grow to about $183.4 Billion in 2024. Dental disease is also a major cause of economic and social loss for individuals and countries. In 1996, oral disease is estimated to have resulted in 2.4 million days of work and 1.6 million days of school lost in the US. It is estimated these indirect costs increase the total economic burden by 50%. Adults and children in low socioeconomic classes have more untreated dental caries because the cost of treatment is prohibitive.

If active carious lesions can be diagnosed before irreversible cavitation, the patient and dentist can be alerted to improve dental hygiene in specific regions of the mouth. Carious lesions initially form when bacteria in the dental biofilm on a tooth surface ferment sugars and produce acids, which demineralize enamel resulting in an initial white-spot lesion. However, the process is dynamic and early lesions called "microcavities" or incipient carious lesions are reversible via remineralization using calcium and phosphorous in saliva, aided by the presence of fluoride in drinking water and toothpaste (see B. Clarkson, "Redistribution of enamel fluoride during white spot lesion formation: an in vitro study on human dental enamel," Caries Res. 1981, 15). Conservative dental treatments that arrest or reverse the demineralization process can be effective at this stage. When adequately remineralized, the tooth surface remains intact. However, if decalcification continues, irreversible cavitation occurs, requiring a dental procedure or invasive surgical restoration.

Caries as referred to herein includes various stages of enamel demineralization and bacterial decay of a tooth, including initial microscopic increases in pore size in the tooth enamel (e.g., microcavity development) to extensive decay and cavities leading to severe loss of tooth structure and eventually loss of the tooth. The characteristic feature of active carious lesions in enamel with decalcification, when dry, is a white and rough surface. This indicates an increase in microscopic pore size of the enamel. An active lesion is one that is progressing toward cavitation (demineralizing) and may be considered to have a slightly decalcified (approximately 5% compared to normal enamel) microporous surface, overlying a subsurface lesion that may have porosity of 30-40% (see B. Clarkson, et al., "Redistribution of enamel fluoride during white spot lesion formation: an in vitro study on human dental enamel." Caries Res. 1981, 15.). Subsurface demineralization may eventually cause collapse of the overlying tooth surface, creating cavitation. An inactive lesion is not progressing because the porosity, particularly on the exposed surface, has been reduced by mineral and/or protein deposition, thus facilitating conservative management. Generally inactive lesions require no treatment while active lesions do. Early active lesions permit conservative remineralization treatment, while cavitated lesions require invasive dental restoration.

The ability to diagnose caries at an early stage of development can be advantageous as early treatment can reverse formation of cavities. However, conventional methods of detecting caries have been inadequate or even harmful and commonly occur far too late in the development of caries/cavities to reverse or diminish further damage.

In certain aspects, the present disclosure provides an oral care composition for detecting one or more carious lesions in teeth in the oral cavity of a subject. The oral care composition may be administered to the subject for detection and diagnosis of the presence of one or more carious lesions. The subject may be a human, companion animal, such as a cat, dog, or horse, and the like. The oral care composition may comprise a component or a nanoparticle. The composition has at least one cationic region or a net positive charge that is capable wherein the composition has a cationic moiety or a net positive charge, which is capable of indicating the presence of one or more carious lesions when component or nanoparticles are associated therewith. The component or nanoparticle may comprise a biocompatible, bio-based, and/or biodegradable polymer bearing at least one cationic region or having a net positive charge that is capable of associating with one or more caries or carious lesions on a tooth in an oral cavity of a subject. The component or nanoparticle also comprises an imaging agent, an active ingredient (e.g., a therapeutic agent), or combinations thereof. An imaging agent may be optionally bonded to the biocompatible, bio-based and/or biodegradable polymer. As will be discussed below, the oral care composition may further comprise an oral care carrier or delivery vehicle.

In certain aspects, the component or nanoparticle can indicate the presence of one or more carious lesions when the component or nanoparticle is associated with the one or more carious lesions on the subject's tooth. In other aspects, the component or nanoparticle is capable of treating one or more carious lesions when the component or nanoparticle is associated therewith on the subject's tooth. In certain other aspects, the component or nanoparticle is thus capable of indicating the presence of one or more carious lesions and treating the one or more carious lesions when the component or nanoparticle is associated therewith. The oral care composition further comprises an orally acceptable carrier.

In certain variations, the present disclosure provides nanoparticles for oral administration that may be diagnostic components for detecting one or more carious lesions in teeth in the oral cavity of a subject. An oral care composition comprising the nanoparticles may be administered to the subject for detection and diagnosis of the presence of one or more carious lesions. As will be discussed below, the nanoparticle may be incorporated into an oral care composition that further comprises an oral care carrier or delivery vehicle. The nanoparticle comprises a biocompatible and biodegradable polymer bearing at least one cationic region (e.g., having a positive charge). In certain other aspects, the nanoparticle may exhibit an overall net positive charge. The nanoparticle also comprises an imaging agent associated with (for example, by bonding) the biocompatible and biodegradable polymer.

If active carious lesions can be diagnosed before irreversible cavitation, the patient and dentist can be alerted to improve dental hygiene in specific regions of the mouth and initiate remineralization strategies.

The ability to differentiate between inactive and active carious lesions can be very helpful in monitoring caries progression following treatment using remineralization, in order to enable the dentist and dental patient to implement conservative treatment strategies, avoiding more invasive and expensive restorative procedures, such as "drill and fill" or other invasive procedures, as well as ability to reduce patient exposure to harmful radiation from taking X-ray images, which may especially be undesirable in children.

As explained above, as opposed to inactive lesions which have a closed surface, the characteristic feature of active carious lesions in the enamel is a white and rough surface (also known as a "white spot lesion"), combined with surface porosity that provides access to the active lesion. Furthermore, the internal surfaces of active carious lesions have a negative surface charge. Consequently, the overall net charge or cationic regions of the nanoparticles according to the present teachings provide the ability to target one or more of these lesions of the tooth by electrostatic attraction and adsorption onto the exposed surfaces of these lesions.

Thus, a biocompatible, biodegradable, and/or bio-based polymer has at least one cationic region (e.g., having a positive charge) capable of selectively associating with one or more carious lesions that have a negative surface charge on a tooth in an oral cavity of a subject. The nanoparticle comprises at least one imaging agent that enables detection of the particle after being administered and after the nanoparticle associates with the one or more carious lesions regions on the tooth.

By "biocompatible," it is meant that a material or combination of materials can be in contact with cells, tissue in vitro or in vivo, or used with a subject (such as mammals or other organisms) and has acceptable toxicological properties for contact and/or beneficial use with such cells, tissue, and/or animals. For instance, a biocompatible material may be one that is suitable for administration in a subject without adverse consequences, for example, without substantial toxicity or acute or chronic inflammatory response and/or acute rejection of the material by the immune system, for instance, via a T-cell response. It will be recognized, of course, that "biocompatibility" is a relative term, and some degree of inflammatory and/or immune response is to be expected even for materials that are highly compatible with living tissue. However, non-biocompatible materials are typically those materials that are highly toxic, inflammatory and/or are acutely rejected by the immune system, e.g., a non-biocompatible material implanted into a subject may provoke an immune response in the subject that is severe enough such that the rejection of the material by the immune system cannot be adequately controlled, in some cases even with the use of immunosuppressant drugs, and often can be of a degree such that the material must be removed from the subject. In certain aspects, biocompatible materials are those that are approved for use in humans by an appropriate regulatory agency, such as the Federal Drug Administration (FDA) in the United States; the European Commission (EC)/European Medicines Agency (EMEA) in Europe; or Health Products and Food Branch (HPFB) in Canada.

By "biodegradable," in certain aspects, the material dissolves or disintegrates at different rates ex vivo or in vivo. Dissolving refers to physical disintegration, erosion, disruption and/or dissolution of a material and may include the resorption of a material by a living organism. The polymeric material forming the nanoparticle may dissolve or disintegrate at different rates or have different solubility (e.g., aqueous solubility) that impacts the rate of dissolution. The materials can dissolve or erode upon exposure to a solvent comprising a high concentration of water, such as saliva, serum, growth or culture media, blood, or bodily fluids. Disintegration may also include the material breaking into small pieces, which may collectively form a colloid or gel. In certain variations, the nanoparticle or component degrades in a time period of greater than or equal to about 30 minutes. In other variations, the nanoparticle or component may degrade in less than or equal to about 30 days after introduction into the oral cavity and exposure to saliva. An oral composition may have a degradation time of greater than or equal to about 30 minutes to less than or equal to about 30 days after introduction into the oral cavity.

As an example of biodegradation, saliva which contains the natural enzyme amylase may act upon starch to cleave the glycosidic linkages and reduce its high molecular weight (MW) structure to result in low MW water-soluble mono- and oligo-saccharides and sugars.

In certain aspects, the material may be "bio-based," meaning that at least a substantial portion, for example 50% or more, of a material is made from one or more substances derived from living or once-living organisms. A bio-based material may comprise biopolymers, which are polymers produced by living organisms or derived from polymers produced by living organisms.

The nanoparticle thus comprises a polymer, such as a biocompatible, biodegradable, and/or bio-based polymer, bearing at least one cationic region (e.g., having a positive charge). In certain aspects, the at least one cationic surface region on the nanoparticle has a zeta potential value at the pH of saliva (a pH of about 7) that is greater than or equal to about 0 to less than or equal to about +50 mV, optionally greater than or equal to about +2 mV to less than or equal to about +30 mV, and in other variations greater than or equal to about +5 mV to less than or equal to about +20 mV. In certain variations, the nanoparticle having such ranges of zeta potential is thus capable of associating with one or more carious lesions on the surface of a tooth having a negative charge. In other aspects, the nanoparticles or components may have a net positive charge of less than or equal to about 30 mV or optionally less than or equal to about 20 mV. In certain variations, the nanoparticle or component may have a net positive charge and/or a zeta potential corresponding to any of the values specified above. In one variation, the nanoparticle or component may have a net positive charge and/or a zeta potential at greater than or equal to about +2 mV at a pH of 7.

Without intending to be limited by any particular theory, it is believed that active carious legions have a negative charge. The process of de-mineralization releases free ions, such as calcium ions and magnesium ions, many of which are cationic. Release of these ions appears to result in the remaining de-mineralized surface having a negative charge. A compound or nanoparticle having cationic moieties or a net positive charge, for example of +2 mV or more, is attracted to the active lesion. However, some studies with other positively-charged nanoparticles (for example gold nanoparticles and lipid nanoparticles) have found that particles with a higher positive charge, for example a zeta potential of +38 mV, had some toxic effects. While other studies have shown no toxic effect with such positively-charged nanoparticles, in certain aspects, nanoparticles used in accordance with certain aspects of the present disclosure have only a moderate positive charge, for example, less than or equal to about 30 mV or optionally less than or equal to about 20 mV. The components or nanoparticles are optionally water-soluble or dispersible.

In certain aspects, the composition has a cationic moiety or a net positive charge. Thus, a component may be a material comprising a compound having cationic moieties or a net positive charge, like a functionalized starch-based compound by way of example, which is used for oral administration and is capable of associating with one or more carious lesions on a tooth. In other aspects, a nanoparticle is provided, which may comprise the same compound (e.g., a functionalized starch-based compound) so that the nanoparticle thereby also has cationic moieties or a net positive charge so that it is capable of associating with one or more carious lesions on a tooth. Alternatively, a nanoparticle may comprise one or more of a polymer, an imaging agent, and an active ingredient (e.g., a therapeutic agent), where one or more of these constituents has a negative charge, but the nanoparticle still exhibits a net positive charge or cationic moieties capable of associating with an active carious lesion on a tooth.

In certain aspects, the biocompatible and biodegradable polymer is itself cationic or may be a copolymer comprising cationic domains. In other variations, the biocompatible and biodegradable polymer is reacted with a cationic moiety to create the one or more cationic regions on the surface of the nanoparticle. Such a bond may be a covalent bond or an ionic bond. In certain aspects, the bond is a covalent bond between the cationic moiety and the biocompatible and biodegradable polymer. The nanoparticle may be zwitterionic and include both positively charged regions and negatively charged regions.

In certain variations, the biocompatible and biodegradable polymer may be a polymer selected from the group consisting of: a mono-, oligo-, or polysaccharide, carboxymethylcellulose, a polymeric starch, dextrin, dextran, cellulose, chitosan, gelatin, polyethyleneimine (PEI), poly(L-lysine) (PLL), poly(L-arginine), poly(amidoamine) (PAA), poly(amino-co-ester) (PAE), poly(2-N,N-dimethylaminoethylmethacrylate) PDMAEMA, poly(4-vinylpyridine) (P4VP), polyesters, poly(acrylic acid), poly(methacrylic acid), a polyalkylene glycol, a methyl vinyl ether/maleic anhydride copolymer, combinations and equivalents thereof. Exemplary starches include amylose or amylopectin.

Where the biocompatible and biodegradable polymer is itself a cationic polymer, it may be selected from the group consisting of: a cationic or cationically modified mono-, oligo-, or polysaccharide, carboxymethylcellulose, starch, dextrin, dextran, chitosan, cellulose, gelatin, polyethyleneimine (PEI), poly(L-lysine) (PLL), poly(L-arginine), poly(amidoamine) (PAA), poly (amino-co-ester) (PAE), poly(2-N,N-dimethylaminoethylmethacrylate) PDMAEMA, poly(4-vinylpyridine) (P4VP), combinations and equivalents thereof. In certain variations, the biocompatible polymer may comprise an amine, such as a tertiary amine or a quaternary amine. In other variations, the biocompatible and biodegradable polymer comprises a reaction product of glycidyl trimethyl ammonium chloride bonded to the biocompatible and biodegradable polymer. In yet other variations, the biocompatible polymer may be zwitterionic.

In other variations, the cationic region on the nanoparticle comprises a cationic moiety bonded with the biocompatible and biodegradable polymer. In certain variations, the cationic moiety may comprise an amine, such as a tertiary amine or a quaternary amine, or a zwitterionic group. In one variation, the cationic moiety is a reaction product of glycidyl trimethyl ammonium chloride bonded to the biocompatible and biodegradable polymer. In one embodiment, a nanoparticle is fabricated that comprises starch nanoparticles having a particle size ranging of greater than or equal to about 20 nm to less than or equal to about 250 nm. As will be discussed further below, the starch nanoparticle is then modified to include a cationic moiety comprising a reaction product of glycidyl trimethyl ammonium chloride.

The term "nano-sized" or "nanometer-sized" as used herein is generally understood to be less than or equal to about 1 micrometer (i.e., 1, 000 nanometers). Thus, the nanoparticle has at least one spatial dimension that is less than about 1 optionally less than or equal to about 750 nm, optionally less than about 500 nm, and in certain aspects, less than about 200 nm. In certain aspects, all spatial dimensions of the nanoparticle component are less than or equal to about 1 μm (1,000 nm).

In certain aspects, the nanoparticles of the present disclosure have an average particle size or diameter of less than or equal to about 1,000 nm. In certain aspects, the average diameter of the nanoparticle may be greater than or equal to about 1 nm to less than or equal to about 1,000 nm, optionally greater than or equal to about 10 nm to less than or equal to about 1,000 nm, optionally greater than or equal to about 20 nm to less than or equal to about 1,000 nm, optionally greater than or equal to about 30 nm to less than or equal to about 1,000 nm, optionally greater than or equal to about 50 nm to less than or equal to about 1,000 nm, optionally greater than or equal to about 100 nm to less than or equal to about 1,000 nm, optionally greater than or equal to about 10 nm to less than or equal to about 900 nm, optionally greater than or equal to about 100 nm to less than or equal to about 900 nm, optionally greater than or equal to about 10 nm to less than or equal to about 800 nm, optionally greater than or equal to about 100 nm to less than or equal to about 800 nm, optionally greater than or equal to about 10 nm to less than or equal to about 500 nm, optionally greater than or equal to about 100 nm to less than or equal to about 500 nm, optionally greater than or equal to about 10 nm to less than or equal to about 300 nm, optionally greater than or equal to about 50 nm to less than or equal to about 300 nm, optionally greater than or equal to about 100 nm to less than or equal to about 300 nm, and in certain variations, optionally greater than or equal to about 200 nm to less than or equal to about 300 nm. It should be noted that a component used in the oral care composition may have at least one dimension within the same ranges listed above for the nanoparticle.

In some aspects, the nanoparticles may have an average size that is less than the size of the pores on the surface of an active lesion. The size of such pores may vary, but are generally in the range of 500 nm. Accordingly, an average particle size of the nanoparticle may be less than or equal to about 500 nm.

For example, the nanoparticles may be made by a process comprising a) preparation of a first phase comprising a dispersion of starch in water, b) preparation of a dispersion or emulsion of the first phase in a second liquid phase, c) cross-linking of the starch present in the first phase; and d) separation the starch particles thus formed, or another process, such as that described in U.S. Pat. No. 6,755,915. In some examples, nanoparticles produced by such methods are estimated to have a particle size of less than 600 nm.

Nanoparticles include particles optionally made up either partially or entirely of organic materials. In certain aspects, nanoparticles may partially or entirely comprise cross-linked polymers, which might, in some cases, be a single molecule.

The nanoparticle may have a round shape (e.g. a sphere or spheroid shape) or may have a variety of other shapes, such as discs, platelets, rods, and the like.

Without being limited or bound by any particular theory, waxy starch-based nanoparticles might, in some cases, be made up entirely or partially of one or more non-crosslinked molecules given that amylopectin is a highly branched and high molecular weight polymer, and that certain crosslinkers may be reversible in water, especially at low concentrations.

The nanoparticle may be a regenerated starch particle. By "regenerated," it is meant that the particle is formed by partially or completely destroying the crystalline structure of native starch granules, for example by heating and/or thermo-mechanical processing, and re-combining the products by physical aggregation and/or crosslinking. For example, nanoparticles may be made by plasticizing starch using shear forces, optionally in an extruder, and optionally adding a crosslinker during the processing. Examples of such processes are described in U.S. Pat. No. 6,677,386, U.S. Pub. No. 2011/0042841; Delong Song et al., Carbohydrate Polymers 85 (2011) 208-214; PCT International Publication No. WO 2011/071742 A2; U.S. Pat. No. 6,755,915; PCT International Publication No. WO 2010/084088; and PCT International Publication No. WO 2010/065750. Alternatively, fragmented particles may be used. GB 1420392, for example, describes a method of producing fragmented starch particles by cross-linking starch prior to extrusion.

In some variations, the nanoparticles are made according to a process described in U.S. Pat. No. 6,677,386 and U.S. Pub. No. 2011/0042841. In this process, a biopolymer, such as starch, is combined with one or more plasticizers. This combination is mixed under high shear forces, for example, in a twin screw fully intermeshing co-rotating extruder, to plasticize the biopolymer and create a thermoplastic melt phase in which the crystalline structure of the biopolymer is removed. A crosslinking agent is added to the extruder, while mixing continues, to form crosslinked starch-based nanoparticles. The nanoparticles exit the extruder as a strand of extrudate, which is ground to a fine dry powder. The nanoparticles are present in the powder in an agglomerated form, and can be dispersed in an aqueous medium. Particular examples of nanoparticles made by this process include commercially available ECOSPHERE™ nanoparticles available from EcoSynthetix Inc. of Burlington, Ontario, Canada.

In certain variations described herein, a cationic moiety and an imaging or therapeutic agent are chemically bonded to the same polymer, so that a compound may be used that is not in the form of a nanoparticle, but rather may be considered to be a component in the composition. For example, because the reactions described herein for making a nanoparticle cationic and bonding a fluorescent agent to the nanoparticle both involve bonding to starch-based polymers within the nanoparticle, similar reactions can be performed on a soluble form of starch, such as cooked starch, cold soluble starch, pre-gelatinized starch, or a lower molecular weight starch derivative such as dextrin or dextran, other oligomeric or polymeric carbohydrates or other polymers having units. For example, the polymer may comprise glucose repeat units. In other aspects, the polymer comprises hydroxy groups. It should be noted, however, that an embodiment employing a soluble compound (as opposed to a dispersible nanoparticle) may be more difficult to provide in a stable aqueous composition; may have limited ability to carry an active agent (e.g., on a mass of active agent per mass of compound basis); or may not preferentially associate with more porous active lesions (as opposed to less porous inactive lesions) to the same extent as a nanoparticle does. Accordingly, in certain preferred aspects, a nanoparticle is used in an aqueous dispersion or solution. In other variations, a component (e.g., a compound) used in an aqueous dispersion or solution may have an average size of greater than or equal to about 1 nm or optionally greater than or equal to about 10 nm The imaging agent may be a variety of diagnostic or imaging agents that permit detection when delivered to an oral cavity of a subject. In certain variations, one or more imaging agents may be used. The imaging agent on the nanoparticle or component may be capable of detection by visual inspection of the oral cavity with the human eye using a dental curing lamp, for example, by a dental clinician, dental assistant or hygienist. In certain variations, the visual inspection comprises use of an optical filter. The optical filter may be a pair of UV-filtering glasses worn by the clinician, assistant, or hygienist. Thus, the imaging agent may be capable of detection by visual inspection or digital photography of the oral cavity while shining a dental curing lamp (exposing the oral cavity and tooth to electromagnetic from the lamp) on the imaging agent. In other aspects, the visual inspection or digital photography comprises use of an optical filter or filtering of the digital image.

The imaging agent is associated with the biocompatible and biodegradable polymer. In certain aspects, the imaging agent is bonded to the polymer. The imaging agent may comprise a fluorophore that fluoresces in response to electromagnetic radiation from a commercially available standard dental curing lamp that typically emits blue light. Such dental curing lamps typically emit electromagnetic radiation having a wavelength of greater than or equal to about 350 nm to less than or equal to about 600 nm, optionally greater than or equal to about 400 nm to less than or equal to about 500 nm, and in certain variations, greater than or equal to about 430 nm to less than or equal to about 480 nm. In one variation, the fluorophore comprises a fluorescein molecule that is covalently conjugated to the biocompatible and biodegradable polymer. Fluorescein is a suitable fluorophore due to its understood safety and low toxicity. However, a variety of fluorescent tags may be used for diagnostic purposes, including rhodamine, and Alexa FLUO® fluorodyes sold by Molecular Probes, Inc.

Other imaging agents are also contemplated as being bonded to or included (e.g., dispersed within) the biocompatible and biodegradable polymer. In one variation, the imaging agent comprises at least one biocompatible dye or colorant. In certain aspects, one or more biocompatible dyes may be used. In certain embodiments, colorants, pigments, or dyes are optionally selected which are approved for incorporation into a food, drug, or cosmetic by a regulatory agency, such as FD&C or D&C pigments and dyes approved by the Federal Drug Administration (FDA) for use in the United States. Biocompatible dyes and pigments include natural colors, including by way of non-limiting example, caramel coloring (E150), annatto (E160b), green dye from chlorella algae (E140), cochineal (E120), betanin extracted from beets, turmeric (E100), saffron (E160a), paprika (E160c), iron oxides (E172) and Elderberry juice. Other biocompatible dyes and pigments include biocompatible synthetic colors and lakes and dyes. Such food-safe and/or cosmetically acceptable colorants among those useful herein include FD&C Red No. 3 (sodium salt of tetraiodofluorescein), FD&C Red No. 40 (2-naphthalenesulfonic acid), Food Red 17, disodium salt of 6-hydroxy-5-{(2-methoxy-5-methyl-4-sulphophenyl)azo}-2-naphthalenesulfonic acid, Food Yellow 13, sodium salt of a mixture of the mono and disulphonic acids of quinophtalone or 2-(2-quinolyl) indanedione, FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-4-3,5-cyclohexadienimine], FD&C Blue No. 1 (disodium salt of dibenzyldiethyl-diaminotriphenylcarbinol trisulfonic acid anhydrite), FD&C Blue No. 2 (sodium salt of disulfonic acid of indigotin), and mixtures thereof in various proportions. In certain aspects, the colorant comprises a cosmetically and/or pharmaceutically acceptable water insoluble inorganic pigment, such as titanium dioxide, chromium oxide green, phthalocyanine green, ultramarine blue, ferric oxide, or a water insoluble dye lake, including but not limited to aluminum lakes. In certain embodiments, dye lakes include calcium or aluminum salts of an FD&C dye such as FD&C Green #1 lake, FD&C Blue #2 lake, D&C Red #30 lake and FD&C Yellow #15 lake. In yet other embodiments, a white colorant is used, for example titanium dioxide ($TiO_2$), titanium dioxide coated mica, a mineral, or a clay. Combinations of any of these colorants or dyes may also be used.

As such, in certain variations, the present disclosure contemplates a starch-based fluorescently-labeled nanoparticle that targets white lesion spot enamel lesions that may correspond to early stage caries. The starch-based chemistry makes the nanoparticles non-toxic and biodegradable by salivary amylase. Using fluorescein as the fluorophore imaging agent on the nanoparticle, carious lesions can be illuminated and identified using a dental curing lamp, commonly used in most dental offices, which emits a blue light.

Targeted fluorescent imaging nanoparticles can specifically illuminate carious lesions, improving visual contrast, and aiding with diagnosis. The nanoparticles according to certain aspects of the present disclosure are inexpensive, biodegradable in the mouth/oral cavity, non-toxic, and fit in-line with current dental practices (e.g., only requiring visual inspection and/or a dental curing lamp for imaging). In certain aspects, nanoparticle comprises a biopolymer with a cationic charge and an imaging agent.

In certain aspects, the nanoparticle comprises an imaging agent at about 0.1% to less than or equal to about 10% by weight of the nanoparticle.

In certain embodiments, the nanoparticles of the present disclosure may be diagnostic, meaning that they include an imaging agent that reveals the presence of one or more possible caries on or in a tooth in the oral cavity of a subject. In other variations, the nanoparticles of the present disclosure may be therapeutic or diagnostic and therapeutic. Therapeutic nanoparticles may comprise at least one oral care active ingredient. In certain variations, a composition may comprise a first plurality of diagnostic nanoparticles and a second plurality of therapeutic nanoparticles comprising an oral care active ingredient. In certain variations, where the nanoparticle serves a diagnostic, it desirably degrades in a time period of greater than or equal to about 30 minutes and optionally less than or equal to a few hours, for example, to provide the ability for a dental clinician, assistant, or hygienist, to complete the diagnostic procedure and evaluation. In other variations, where the nanoparticle serves a therapeutic role, the nanoparticle may be designed to have a much longer period for degradation, for example, degrading in greater than or equal to about 24 hours to less than or equal to about 30 days or even longer after introduction into the oral cavity and exposure to saliva. This permits the active ingredient to be delivered to the oral cavity (e.g., to a region within or adjacent to carious lesions in a tooth) over a longer time frame to provide therapeutic benefits.

An oral care active ingredient may be used for the prevention or treatment of a condition or disorder of hard or soft tissue of the oral cavity, including but not limited to oral cancer and dry mouth, the prevention or treatment of a physiological disorder or condition, or may provide a cosmetic benefit. Optional oral care active ingredients include an anticaries agent, a remineralizing agent, an antibacterial agent, an anticalculus agent, a tartar control agent, a tooth desensitizer, and combinations thereof, by way of non-limiting example. While general attributes and properties of each of the above categories of actives may differ, there may some common attributes and any given material may serve multiple purposes within two or more of such categories of actives.

In certain variations, the oral care active ingredient comprises an anticaries agent, a remineralizing agent, an antibacterial agent, an anticalculus agent, and combinations thereof. In certain variations, the nanoparticles may be used to identify dental caries, microcavities, or enamel lesions; reduce or inhibit early enamel lesions or microcavities; reduce or inhibit formation of dental caries or cavities; reduce or inhibit demineralization and promote remineralization of the tooth; protect teeth from cariogenic bacteria; inhibit microbial biofilm formation on the tooth or in the oral cavity; and/or reduce levels of acid-producing bacteria in the oral cavity. Oral care actives that are useful herein are optionally present in the compositions of the present invention in safe and effective amounts. In certain aspects, the nanoparticle comprises an oral care active ingredient of about 0.1% to less than or equal to about 50% by weight after incorporation into the nanoparticle, and optionally about 0.1% to less than or equal to about 15% by weight of the oral care active ingredient after incorporation into the nanoparticle.

In certain variations, the oral care active ingredient comprises an anti-caries agent, such as an anti-caries fluoride-containing component that provides fluorine ions in the oral cavity. The fluoride-containing active ingredient may be present at greater than or equal to about 0.02% to less than or equal to about 2.2% by weight after incorporation into the nanoparticle. The fluoride-containing component may be selected from the group consisting of: fluorohydroxyapatite, stannous fluoride, sodium fluoride, calcium fluoride, silver fluoride dehydrate, sodium monofluorophosphate, difluorosilane, combinations and equivalents thereof.

In other variations, the oral care active ingredient comprises a calcium-containing component that provides calcium ions in the oral cavity for remineralizing the tooth. The calcium-containing active ingredient component may be present at greater than or equal to about 1% to less than or equal to about 5% by weight after incorporation into the nanoparticle. The calcium-containing active ingredient may be calcium lactate.

In certain other variations, the oral care active ingredient comprises a calcium and phosphate-containing component for remineralizing the tooth. The calcium and phosphate-containing component optionally comprises calcium glycerophosphate, dicalcium phosphate, tricalcium phosphate, calcium sodium phosphosilicate, or combinations and equivalents thereof. In certain variations, calcium glycerophosphate may be present in the nanoparticle at greater than or equal to about 0.1% to less than or equal to about 1% by weight after incorporation into the nanoparticle. In other variations, dicalcium phosphate may be present in the nanoparticle at greater than or equal to about 2% to less than or equal to about 50% by weight after incorporation into the nanoparticle, optionally greater than or equal to about 2% to less than or equal to about 10% by weight after incorporation into the nanoparticle. In yet other variations, tricalcium phosphate may be present in the nanoparticle at greater than or equal to about 1% to less than or equal to about 5% by weight after incorporation into the nanoparticle. In other variations, calcium sodium phosphosilicate may be present in the nanoparticle at greater than or equal to about 1% to less than or equal to about 10% by weight after incorporation into the nanoparticle.

In other aspects, the nanoparticle may comprise an oral care active ingredient selected from the group consisting of: amine fluoride, casein phosphopeptide, phosphoprotein, and equivalents and combinations thereof. In certain aspects, the nanoparticle may comprise an amine fluoride present in the nanoparticle at greater than or equal to about 0.2% to less than or equal to about 2.2% by weight after incorporation into the nanoparticle. In other aspects, casein phosphopeptide may be present in the nanoparticle at greater than or equal to about 1% to less than or equal to about 5% by weight after incorporation into the nanoparticle. In yet other aspects, phosphoprotein may be present in the nanoparticle at greater than or equal to about 0.001% to less than or equal to about 0.01% by weight after incorporation into the nanoparticle.

In certain variations, the nanoparticle may be a multiphasic nanoparticle that comprises multiple compositionally distinct compartments. Each compartment may thus comprise distinct material compositions. Multiphasic nanoparticles may have a variety of shapes and may comprise two, three, or more distinct compartments. In certain variations, a first compartment may include the imaging agent (e.g., bonded to a polymer in the first compartment), while the second compartment may have one or more oral care active ingredients. Such multiphasic nano-components may be formed by electrified jetting of materials that comprise one or more polymers, such as that disclosed by Roh et al., "Biphasic Janus Particles With Nanoscale Anisotropy", Nature Materials, Vol. 4, pp. 759-763 (October, 2005), as well as in U.S. Pat. Nos. 7,767,017, 8,043,480, 8,187,708, and in U.S. Publication No. 2012/0045487 and PCT International Publication No. WO 06/137936.

In certain aspects, the present disclosure contemplates an oral care composition for oral administration in an oral cavity of a subject. The oral care composition includes any of the nanoparticles discussed above. The nanoparticle also includes an orally acceptable carrier, meaning a material or combination of materials that are relatively safe for use within a subject while considering the risks versus benefits (e.g., that the benefits outweigh the risks). An orally acceptable carrier may thus be any carrier toxicologically suitable for use in the oral cavity. Selection of specific components of the orally acceptable carrier depend upon the form of the oral care composition, for example, whether the oral care composition is a mouth rinse, dentifrice, gel, paint, or the like. Such orally acceptable carriers include the usual components of dentifrices (e.g., toothpastes and tooth powders), gels, paints, mouth rinses (e.g., such as a mouth wash, spray, or rinse), lozenges, and the like, as are well known to those of skill in the art. In certain variations, the oral care composition is a mouth rinse that facilitates extensive and comprehensive coverage of surfaces of teeth, including interproximal/interdental surfaces where caries often tends to develop.

In various aspects, the orally acceptable carrier used to prepare an oral composition may comprise a water-based phase, which may include alcohols and other components. As recognized by one of skill in the art, the oral compositions may include other conventional oral care composition materials, including by way of non-limiting example, surface active agents, such as surfactants, emulsifiers, and foam modulators, abrasives, humectants, mouth feel agents, viscosity modifiers, diluents, pH modifying agents, sweetening agents, flavor agents, colorants, preservatives and combinations thereof.

The oral care composition comprising the nanoparticles may be administered to the subject and thus introduced into the oral cavity of the subject. The plurality of particles selectively accumulates adjacent to caries on the surface of a tooth and/or within cavities in the tooth corresponding to the one or more carious lesions.

In certain variations, the oral care composition may include multiple distinct types of nanoparticles. Thus, in certain aspects, the plurality of nanoparticles is optionally a first plurality of diagnostic nanoparticles comprising the imaging agent. The oral care composition may thus further comprise a second plurality of therapeutic nanoparticles comprising an oral care active ingredient. In certain aspects, the present disclosure contemplates use of nanoparticles comprising biopolymers to target caries, including microcavities, on a tooth within the oral cavity of a subject.

In certain aspects, the present disclosure provides nanoparticle compositions and metabolites that are non-toxic and resorbable in contrast to certain synthetic polymers that can potentially cause side-effects and toxicity when used in medical diagnostic applications. In various aspects, the nanoparticles have an advantageous size for microcavity diagnosis being of a particle size that permits entry into cavities and lesions in tooth enamel. The nanoparticles according to certain variations of the present disclosure are easy to functionalize, allowing for the attachment of various fluorescent or optical dyes or imaging agents, protective coatings, and control over particle charge. Furthermore, the present technology provides the ability to work in-line with current dental technology without requiring additional equipment purchase or training, for example, using an existing standard dental curing lamp for detection. Furthermore, certain variations of the present disclosure provide nanoparticles that can be manufactured on an industrial scale with high production rates for relatively low cost, compared by many micro and nanoparticle systems that are limited by the ability to scale up production.

Thus, the present disclosure provides use of fluorescent biopolymers in the form of nanoparticles used to aid in diagnosis of microcavities. Starch-based nanoparticles offer a new way to assist dentists in the diagnosis of active carious lesions. These particles are biodegradable, inexpensive, nontoxic and use the currently available technology in the dentist's office. The use of image processing to extract only green light and improve contrast is also a new and unusual finding provided by the present teachings, as discussed further below.

In various aspects, the nanoparticles and oral composition contemplated by the present teachings can be used for one or more of the following applications: administration for diagnosis of cavities in a dental office by a clinician (e.g., dentist, dental assistant, or hygienist), home diagnosis of dental cavities, monitoring a level of tooth degradation in clinical trials, and sustained and highly targeted delivery of therapeutics to one or more regions of a tooth having caries or dental cavities.

In certain other aspects, the present disclosure provides methods of making a nanoparticle for oral administration. The method may include functionalizing a biocompatible and biodegradable polymer with a reactive group capable of reacting with an imaging agent. For example, a reactive functional group may be a carboxyl group on the polymer that reacts with an amine on an imaging particle (e.g., an amine-functionalized imaging agent). Another variation may include reacting an alkyne functional group on the polymer by copper-click chemistry on the corresponding imaging agent. Other variations include use of carbodiimides (EDC) that cause direct conjugation of carboxyls (—COOH) to primary amines (—NH$_2$) without becoming part of the final crosslink (amide bond) between target molecules. N-hydroxysuccinimide (NHS) or its water-soluble analog (Sulfo-NHS) can be included in EDC coupling processes to enhance bonding. Other examples of conjugation chemistries include the reaction of azides with phosphines, thiols with maleimide or vinyl groups, or photoinduced cross-linking of photoreactive groups, such as benzophenone. The biocompatible and biodegradable polymer comprises at least one cationic region capable of associating with one or more carious lesions on or inside a tooth in the oral cavity of a subject. The method may thus include reacting the reactive group on the biocompatible and biodegradable polymer with the imaging agent, so that the nanoparticle bears the imaging agent, which is capable of indicating the presence of one or more carious lesions when the nanoparticle is associated therewith. Any of the biocompatible and biodegradable polymer and imaging agents discussed previously above may be used.

In certain variations, the method may include first functionalizing the biocompatible and biodegradable polymer to have at least one first reactive group capable of reacting with a cationic moiety. For example, a reactive functional group may be a hydroxyl group on the polymer that reacts with an epoxide group on a cationic moiety (e.g., an epoxide-functionalized cationic moiety). Then, the biocompatible and biodegradable polymer is reacted with the cationic moiety so that the biocompatible and biodegradable polymer has at least one cationic region with a positive charge capable of associating with one or more carious lesions on a tooth in an oral cavity of a subject. Any of the cationic moieties (or precursors thereof) discussed previously above may be used in such a method.

In one embodiment, particles are made using starch nanoparticles having a particle size ranging from greater than or equal to about 20 nm to less than or equal to about 250 nm measured using dynamic light scattering (DLS) and nanoparticle tracking analysis (NTA) methods. These particles are then chemically modified to increase functionality. In one embodiment, starch is cationized with a cationic epoxide group moiety (glycidyl trimethylammonium chloride) to imbue positive charge to the polymer. Cationic starch nanoparticles have a moderately positive zeta-potential of +30 mV. This positive charge is believed to help the particles to target active early carious lesions, as discussed previously above.

In another embodiment, nanoparticles may be starch nanoparticles having an average particle size ranging from greater than or equal to about 10 nm to less than or equal to about 250 nm, measured using DLS and NTA methods.

Cationic particles may then be oxidized to create carboxyl functional groups. A process using the water-soluble catalyst TEMPO (2,2,6,6-tetramethylpiperidine-1-oxyl) is preferably used to modify the C6 hydroxyl of the glucopyranose starch polymer unit to a carboxyl, which minimizes the molecular weight reduction of the polysaccharide polymer that is common to other oxidative processes.

Oxidized cationic nanoparticles are measured to have a slight positive zeta-potential of approximately +8.5 mV. The carboxyl functionality is intended to allow attachment of fluorescent molecules, however, it also adds some slight negative charge to the particles. Without being limited or bound to any particular theory, this zwitterionic property is believed to enhance the possible fluorescence signal by allowing self-aggregation of fluorescent particles in active carious lesions.

For the purpose of aiding optical diagnosis of early carious lesions, a fluorescent molecule or marker can be attached to the nanoparticle surface. Some examples include fluorescein, Alexa FLUO® dyes, rhodamine, and the like discussed previously above. In one variation, fluorescein isomer 1 is chosen for its ability to illuminate under the blue light emitted from a standard dental curing lamp and its low toxicity and subsequent use in other dental applications The fluorescein isomer 1 is modified to have an amine functionality which allowed for EDC/NHS coupling to oxidized cationic biopolymers. The number of functional groups on the surface of the nanoparticle and the fluorescent tag concentration relative to the particle concentration may determine the fluorescence intensity of the particles. In one embodiment, this is approximately 20 times less fluorescent than a commercially available fluorescein isothiocyanate (FITC)-dextran (10 k MW) from Sigma Aldrich.

EXAMPLES

Materials: Bio-based nanoparticles are provided by Eco-Synthetix Inc. All chemicals are lab grade and purchased from Sigma Aldrich, unless otherwise noted. These include 2,2,6,6-tetramethylpiperidinyloxy radical (TEMPO), sodium bromide, sodium hypochlorite, isopropyl alcohol, glycidyl trimethyl ammonium chloride (ETA), sodium hydroxide, ethanol, fluoresceinamine isomer 1, EDC, NHS, FITC-dextran (10 k), and fluorescein sodium salt.

Example 1—Chemical Modification

The chemical reaction scheme for modification of starch nanoparticles is presented in FIG. 1, and described further below. All reactions are repeated in triplicate to understand and account for batch-to-batch variability.

Cationization of Starch Nanoparticles

Figure 1:
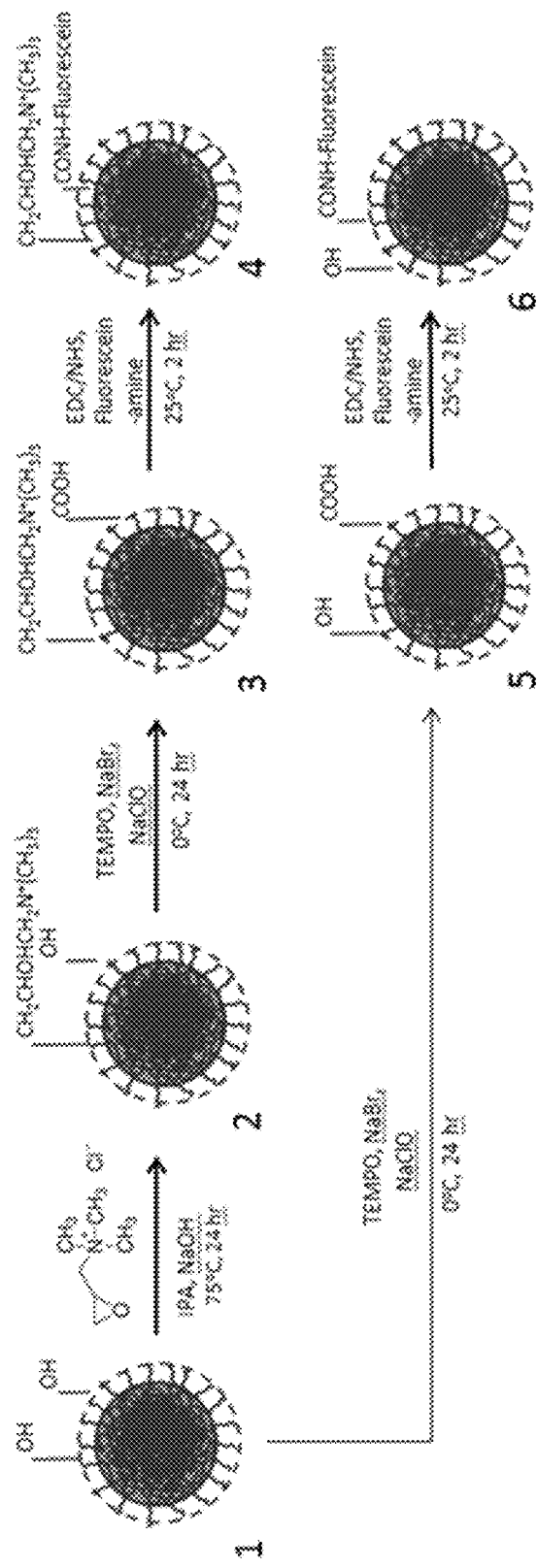

Starch nanoparticles shown at 1 in FIG. 1 are modified to be cationic according to a procedure shown in Huanga Y. et al. "Ultra-small and innocuous cationic starch nanospheres: Preparation, characterization and drug delivery study." *International Journal of Biological Macromolecules*, 58: pp. 231-239 (2013).

Starch nanoparticles are dispersed at 10% solids into 100 mL of 1% sodium hydroxide in DI water. To this solution, 3 mL of isopropyl alcohol and 4.3 g of glycidyl trimethyl ammonium chloride are added, and allowed to mix for one hour. The mixture is then heated to 75° C. overnight, before precipitation in ethanol and centrifugation, followed by lyophilization, yielding cationic starch nanoparticles (shown at 2 in FIG. 1).

TEMPO Oxidation of Starch Nanoparticles

Starch nanoparticles are oxidized according to a procedure shown in Kato, Y. et al., "Oxidation process of water-soluble starch in TEMPO-mediated system," Carbohydrate Polymers 51, pp. 69-75 (2003). Briefly, a 100 mL 5% solution of cationic starch nanoparticles dispersed in DI water is mixed with a 100 mL aqueous solution containing 0.048 g of TEMPO and 0.635 g of sodium bromide. The mixture is put on ice, and the pH is adjusted using a 10% sodium hydroxide solution to bring the pH above 10. 20 g of sodium hypochlorite solution (1:2 molar ratio to StNP) are added slowly to the mixture, while maintaining the pH above 10 using sodium hydroxide. The reaction is left overnight and finished at a pH above 10, at which point it is precipitated in ethanol and separated by centrifugation, followed by lyophilization, yielding zwitterionic starch nanoparticles (shown at 3 in FIG. 1). The same reaction conditions performed on unmodified starch nanoparticles (1 in FIG. 1) yielded anionic particles (shown at 5 in FIG. 1).

EDC/NHS linkage of FITC-amine to —COOH functionality. Carbodiimide (EDC) and other similar carbodiimides are cross-linkers that directly conjugate carboxyls (—COOH) to primary amines (—$NH_2$) without becoming part of the final crosslink (amide bond) between target molecules. N-hydroxysuccinimide (NHS) or its water-soluble analog (Sulfo-NHS) is often included in EDC coupling processes to improve efficiency or to create a more stable, amine-reactive intermediate.

2 g of zwitterionic starch nanoparticles are dissolved in a 20 mL solution of 0.1M MES, 0.5M NaCl buffer. A 10× molar excess of EDC is added (0.2 g) and allowed to mix for 20 minutes, and 1.5× mass of NHS (0.3 g) is added and mixed for 10 minutes. A 20 mL solution of 0.1M PBS, 0.15M NaCl is added to raise the pH above 7. Fluorescein-amine is added at a 1:75 molar ratio (0.05 g), and allowed to react for 2 hours. The particles are precipitated in ethanol, separated by centrifugation, and lyophilized, yielding fluorescein-labeled cationic starch nanoparticles (shown at 4 in FIG. 1). The same reaction conditions using the anionic starch nanoparticles yielded fluorescein-labeled anionic particles (shown at 6 in FIG. 1).

Chemical analysis: FTIR, NMR, and XPS.

Fourier Transform Infrared (FTIR) spectroscopy is completed using a Thermo Scientific Nicolet 6700 instrument. Samples are prepared by spin coating modified starch nanoparticles onto a gold-coated silicon wafer, followed by vacuum drying for 24 hours. 128 scans are taken for each sample.

H'-NMR analysis is completed using a Varian MR400 instrument. Samples are dispersed in D20 at approximately 5% solids and peak analysis is compared to results as previously shown in Kato et al.

X-ray Photon Spectroscopy (XPS) is run on dry powder starch nanoparticle samples using an Axis Ultra X-ray photoelectron spectrometer (Kratos Analyticals, UK) outfitted with a monochromatized Al Kα X-ray source at a power of 150 kW.

Particle Characterization:

Zeta analysis, size analysis, fluorescence analysis.

Starch nanoparticle samples 1-6 are dispersed at 0.025% solids and analyzed by various particle characterization techniques, including zeta potential and DLS analysis using a Malvern ZetaSizer, and Nanoparticle Tracking Analysis (NTA) using a NanoSight NS300.

Particle fluorescence of fluorescein-labeled anionic and fluorescein-labeled cationic StNPs is measured using a BioTek Neo 1 fluorescence plate reader and compared at multiple concentrations against a commercially available FITC-dextran (10 k MW).

Example 2—Fluorescein Loaded Cationic Starch Nanoparticles

Cationic starch nanoparticles are loaded with fluorescein sodium salt by dispersing a mixture of 5% by mass starch particles and 0.25% fluorescein salt, and lyophilizing the solution. The fluorescein anion interacts with the cationic groups on the starch nanoparticle, holding the fluorescent dye within the particle. Particles are approximately 30 nm in size.

Example 3—EHD Jetting of Chitosan

Chitosan powder (degree of deacetylation, 75-85%; molecular weight 190-310 kDa) is dissolved at 1% by weight in trifluoroacetic acid containing 0.05% by mass fluorescein to form a homogeneous solution. Chitosan nanoparticles are prepared by electrohydrodynamic (EHD) jetting using a setup involving a 1 mL plastic syringe, a stainless-steel needle (22 G; inner diameter, 0.413 mm), a syringe pump, a high-voltage power supply, and an aluminum plate placed directly below the needle as the grounded counter electrode (collector). The aforementioned solution can be drawn into the syringe and extruded through the needle at a constant flow rate using the syringe pump. With a high voltage of approximately 10 kV the liquid forms a Taylor cone at the tip of the needle which breaks into droplets which are collected 15 cm from the tip of the needle on the grounded collection plate. The nanoparticles are allowed to dry for 24 hours under vacuum to remove any trace solvent, before being collected by scraping from the aluminum plate and dispersed in water, followed by filtration using a 0.4 micron filter, yielding fluorescently-labeled chitosan nanoparticles, approximately 200-300 nm in size.

Example 4—EHD Jetting of Cationic Starch Nanoparticles

Cationic starch nanoparticles are dispersed at 5% by mass in an 80:20 v:v solution of water:ethanol with 0.25% fluorescein sodium salt. This solution is jetted using an electrohydrodynamic jetting setup as described previously in Example 3, however using a voltage of approximately 16 kV, yields nanoparticles which are approximately 300-500 nm in size.

Example 5—Bicompartmental Jetted Particles for Combined Fluoride Delivery and Fluorescent Diagnosis Bicompartmental starch nanoparticles are prepared by using the same jetting procedure described above by using a setup involving needles placed adjacent to one another. One needle is used for jetting a solution of cationic starch nanoparticles dispersed at 5% by mass in an 80:20 v:v solution of water:ethanol with 0.25% FITC-dextran. The other needle is used for jetting a solution of cationic starch nanoparticles dispersed at 5% by mass in an 80:20 v:v solution of water:ethanol with 1.3% by mass of a 10 k M.W. PEG-diglycidyl ether, and 0.25% by mass of sodium fluoride. Particles are then left for 72 hours at 37° C. to allow the PEG-diglycidyl ether to cross-link the fluoride containing component of the starch to extend release. The final particles are bicompartmental with a fast-degrading fluorescent compartment for caries diagnosis, and a slow degrading fluoride-loaded compartment for remineralization. Particles are approximately 300-500 nm in size.

Example 6—Click-Functionalized Cationic Starch Nanoparticles

Cationic starch nanoparticles are chemically modified by dispersion at 5% by mass solids in dimethyl sulfoxide (DMSO) (Sigma), and addition of 1% by mass DMAP (Sigma) to the solution. Once fully dispersed, 1% by mass glycidyl propargyl ether (Sigma) is added and allowed to react at room temperature for 48 hours, before finishing the reaction by quenching with hydrochloric acid (Sigma). Addition of 50% volume ethanol, allows for precipitation of the starch nanoparticles and removal of the supernatant, and an additional cleaning step and re-precipitation from water:ethanol purifies the particles, which are then dried by lyophilization. The final particles are approximately 20 nm in size, cationic with a zeta potential of approximately +25 mV, and have an alkyne functional group with can be modified by copper-click chemistry.

These particles are then dispersed in water at 5% by mass, and 2M triethylammonium acetate buffer is added, pH 7.0, to a final concentration 0.2 M. The solution is diluted 3:2 with DMSO, before adding a 1.5% by mass solution of Cy5-azide dissolved in DMSO, and vortexed to mix. Ascorbic acid solution is then added to the mixture to make the final concentration 0.5 mM and vortexed briefly, before degassing the solution by bubbling inert gas in it for 30 seconds. Nitrogen, argon, or helium can be used. 10 mM Copper (II)-TBTA Stock in 55% DMSO is added to the mixture, flushed the vial with inert gas and the cap is closed. The solution is then vortexed thoroughly. If significant precipitation of azide is observed, the vial is heated for 3 minutes at 65° C., and vortexed.

The reaction mixture is kept at room temperature overnight, before precipitation using ethanol and centrifugation, followed by lyophilization. Final particles are approximately 20-30 nm in size, with a cationic zeta potential (20-35 mV), and fluorescently labeled with Cy5 fluorophores.

Particle Degradation Study.

Starch particles are dispersed at 1% solids. Half of the particle dispersions are set aside as an initial solution and diluted 1:1 v:v with DI-water. The remaining half of the particle dispersions are taken and added to an equal volume of saliva, and placed in a 37° C. incubator for 30 minutes, as a final dispersion. Saliva is collected and used immediately to minimize potential denaturation of salivary enzymes. Both the initial and final dispersions are tested with iodine and Benedict's reagent.

Iodine Test.

20 microliters of iodine solution are added to 2 mL the initial and final dispersions, and examined for color using ImageJ software.

Benedict's Reagent Test 20 microliters of Benedict's reagent are added to 2 mL of the initial and final dispersions and heated to 80° C. for 30 minutes, and then run under a UV-Vis spectrophotometer to measure absorbance at a wavelength of 735 nm.

Dental Testing.

Preparation of Teeth.

Extracted teeth are obtained from School of Dentistry, University of Michigan (human subjects exempt) and stored in 1% sodium azide before use. The teeth are painted with an acid resistant varnish leaving a 1 mm 2 enamel window on the buccal surface of the crowns of the teeth. The teeth are then immersed in a pH 5.0 demineralization gel containing 0.1 M lactic acid, 4.1 mM $CaCl_2 \cdot 2H_2O$, 8 mM $KH_2PO_4$, and 1% w/v CMC (carboxymethylcellulose sodium) at 37° C. for 8 days (ref: Lippert et al., Caries Res. 46: pp. 23-30 (2012)). At the completion of the demineralization, the teeth are rinsed with distilled $H_2O$ before subjected to caries activity test. Residual varnish is removed by washing in acetone.

Cavity Diagnosis Testing.

1% solutions of FITC-dextran, FITC-anionic StNP, and FITC-cationic StNP, and a 0.001% solution of fluorescein sodium salt are prepared. Teeth are exposed to 20 microliters of sample for three minutes prior to rinsing in DI water. Rinsing is done initially for 10 seconds, and teeth are examined and photographed while illuminated with a standard dental curing lamp. Rinsing is continued for an additional 10 seconds, followed by imaging, and this is repeated for up to 5 minutes to determine "residence times" for each sample to optimize the exposure procedure.

Based on this optimization, it is found that a twenty second rinse in DI water is sufficient to wash away all but the FITC-cationic StNPs, which remained even up to 5 minutes. 15 teeth are divided into 3 groups for testing with each control (FITC-dextran, fluorescein-labeled anionic-StNP, and fluorescein sodium salt). After a 3 minute exposure followed by 20 seconds of rinsing, imaging is performed under the dental curing lamp. The same teeth are then dosed with fluorescein-labeled cationic StNPs and imaged demonstrating the ability of these particles to illuminate the carious lesions that could not be lit by the various controls.

Image Analysis.

Digital images are taken with a Nikon ABC camera and analyzed using ImageJ image analysis software. In particular, the "mean gray value" measurement tool is used to compare grayscale brightness between the carious lesion and the background tooth as a measurement of contrast. In addition, the "split channels" option is used as a second method to extract green pixels from the images, to isolate the fluorescein color.

Two-Photon Microscopy.

Treated teeth are examined using a Leica TCS SP8 2-Photon Confocal with FLIM & FCS using a 40× oil-immersion objective. Samples are immersed in oil and placed on a glass-bottomed petri dish. The illumination wavelength is set to 810 nm, and z-stack images are collected for a variety of tooth samples.

Figure 2:
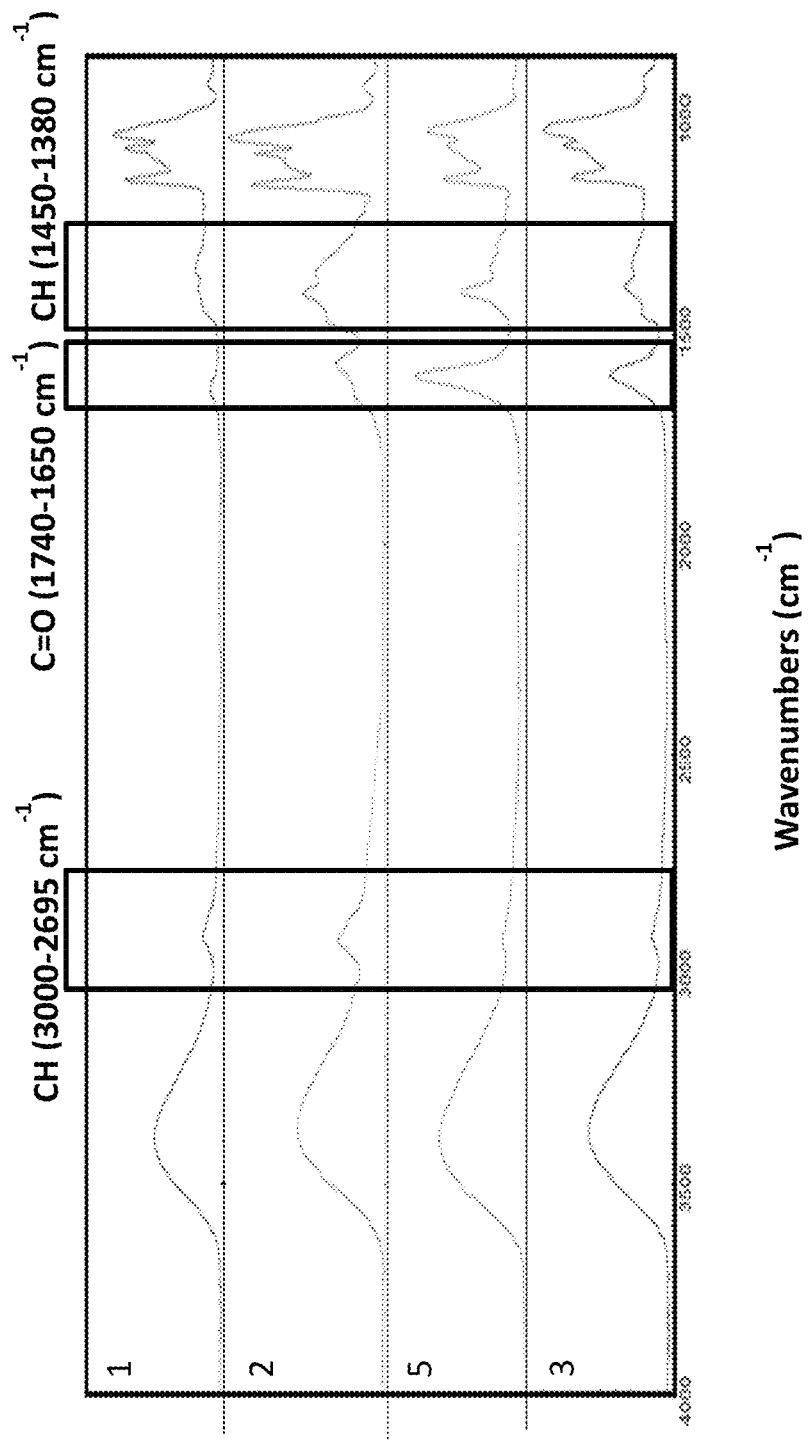

Results and Discussion:

Chemical Modification and Analysis:

The chemical modification of starch nanoparticles is completed using the reaction procedures discussed above and shown in FIG. 1 (steps 1-4). Particles are collected at intermediate steps to produce cationic StNPs, anionic StNPs, and zwitterionic StNPs, in order to analyze the efficacy of the chemical reactions. FTIR results for these particles are shown in FIG. 2. As there are no characteristic NR4 absorptions, comparing the cationic StNPs with unmodified StNPs, only evidence of aldehyde and alkane can be seen. This can be seen with increased peaks at 2930 $cm^{-1}$ (CH alkane), 2830 cm$^{-1}$ (CH aldehyde), 1450 cm$^{-1}$ (CH alkane), and 1390 cm$^{-1}$ (CH aldehyde) and appearance of peaks at 2830 cm$^{-1}$ (CH aldehyde), 1720 cm$^{-1}$ (C═O aldehyde). Considering the anionic StNPs there are sharp increases in absorption peaks at 1710 cm$^{-1}$ (C═O carboxyl) and 1422 cm$^{-1}$ (OH carboxyl). The zwitterionic StNPs show evidence of all of these peaks.

Figures 11A, 11B:
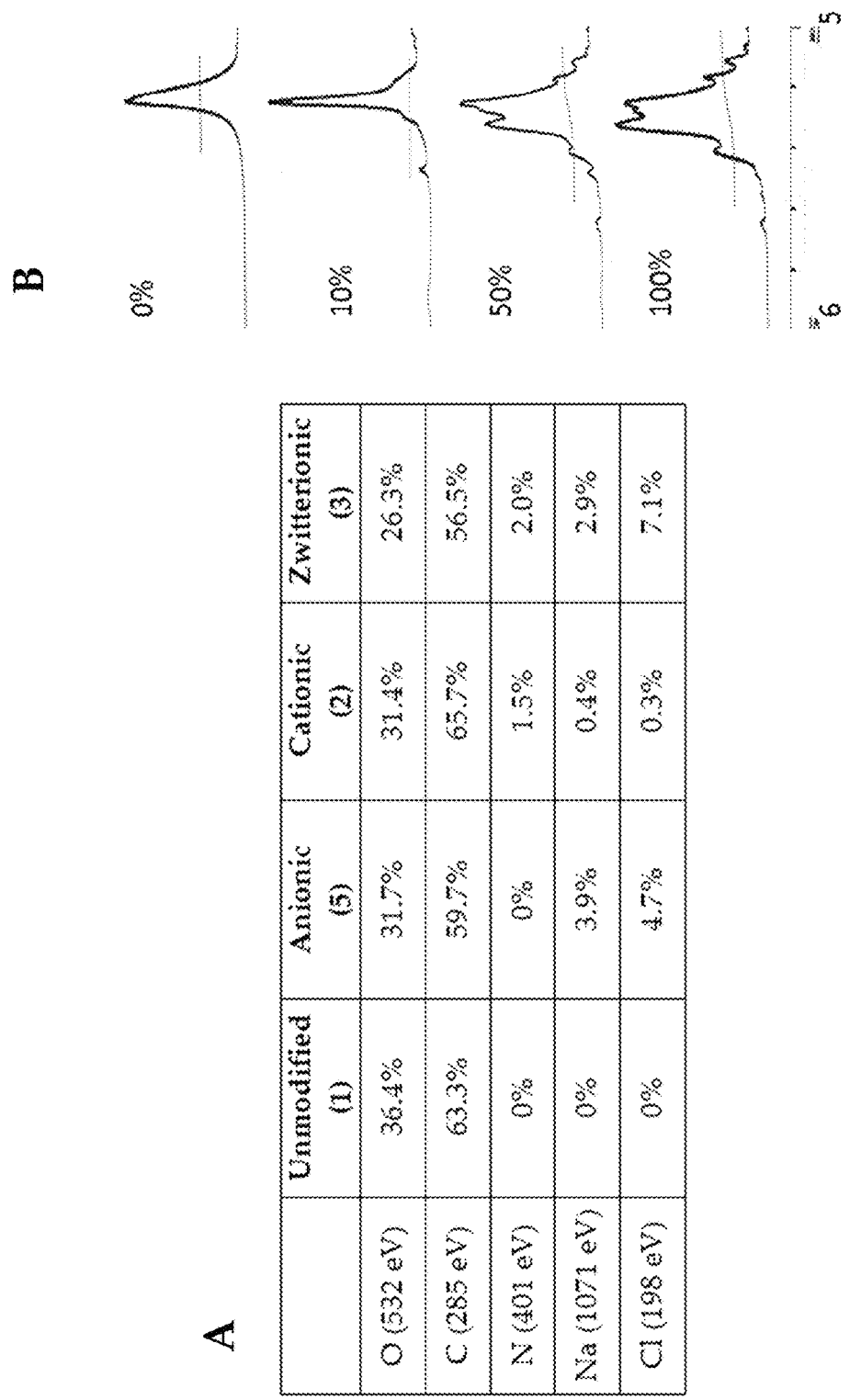

To further validate the cationization reaction, XPS measurements of the samples are taken with results shown in FIG. 11A. These results show the presence of nitrogen after the cationization reaction at approximately 1.5-2 atomic percent, which corresponds to an approximate reaction efficiency of approximately 30%. This result is consistent after TEMPO oxidation of the zwitterionic StNPs. The reaction is likely limited by steric and electrostatic repulsion.

To characterize the TEMPO oxidation reaction, $^1$H NMR analysis is performed as shown in FIG. 11B. The peak shift corresponding to the C6 hydrogen (5.2 to 5.4 ppm) indicated approximately 40% reaction efficiency. Without being limited to or bound by theory, it is hypothesized that the complex gel structure of the starch particles prevents full oxidation by sterically hindering the TEMPO catalyst.

Figure 12:
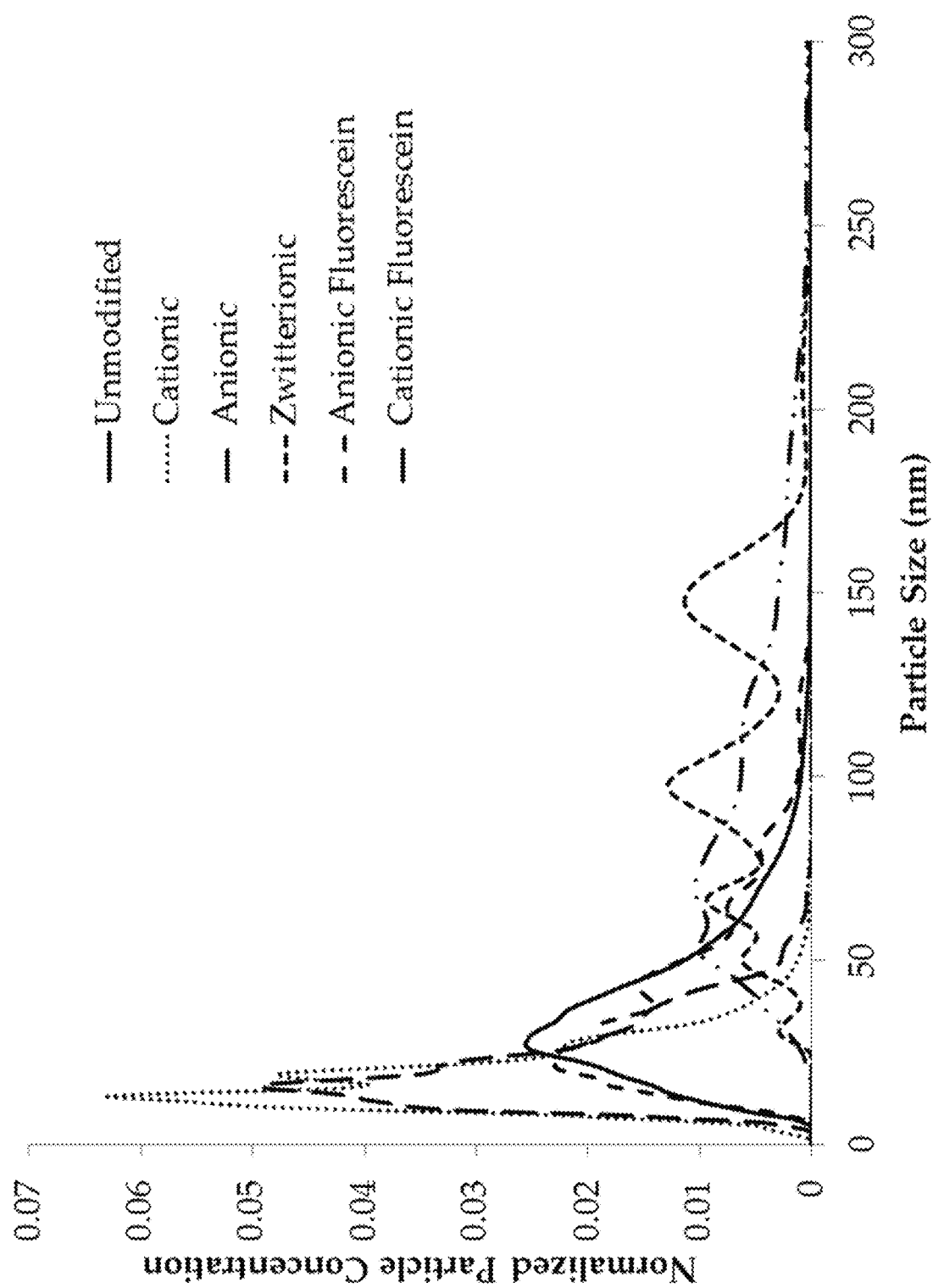
FIG. 12 shows a graphical representation of a Nanoparticle Tracking Analysis (NTA) particle size analysis of modified starch nanoparticle samples prepared according to certain aspects of the present disclosure, showing the particle size distribution for each sample.

In addition to chemical analysis, particle analysis is also performed on these samples, including size analysis by NTA and DLS, and zeta potential measurements, as shown in FIGS. 3A and 12. This grade of unmodified StNPs shows a small particle size and neutral charge. With TEMPO oxidation, particle charge decreased and average particle size decreased significantly. With cationization, particle size decreased and charge increased. When both reactions are combined to make zwitterionic particles, average particle size increased and particles showed a moderate cationic charge. It is expected that the combination of both charges results in slight aggregation due to electrostatic interactions. The addition of fluorescein by EDC-NHS ligandization slightly neutralized the particle charge, and appeared to have no significant impact on particle size.

Particle Degradation Study.

Figures 4A, 4B:
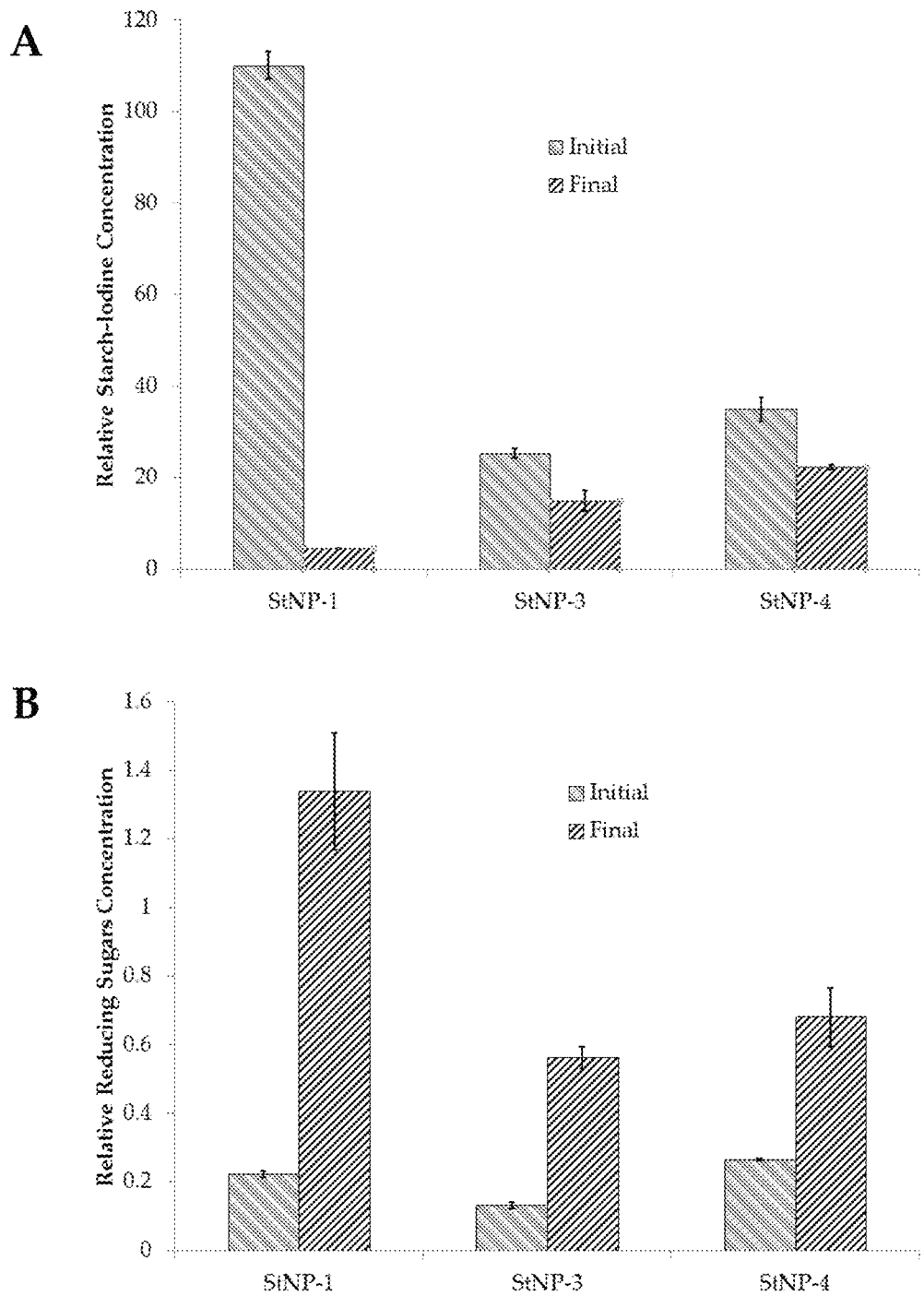

Starch particle degradation is confirmed using the iodine and Benedict's reagent tests, with results shown in FIGS. 3B and 4A-4B. For unmodified, zwitterionic, and fluorescent cationic StNPs, the iodine test showed a decrease in starch staining after 30 minutes of exposure to saliva, while the Benedict's test showed an increase in the presence of reducing sugars. These results indicate that starch particles are degraded into reducing sugars within a 30 minute period of exposure to saliva. Further, there appears to be less intense staining in the modified starch nanoparticles and some initial reducing sugars. This is likely the result of minor degradation during the chemical modification reactions, and possibly because the functionalities somewhat inhibit the ability of iodine to stain the chemically-modified starch. By comparing all of the results in FIGS. 3B and 4A-4B, it can be concluded that the modified starch nanoparticles degrade in the presence of saliva.

Particle fluorescence of the cationic and anionic starch nanoparticles are measured relative to FITC-dextran. It is found that the cationic starch nanoparticles are approximately 20× less fluorescent than FITC dextran, and the anionic starch nanoparticles are approximately 80× less fluorescent than FITC-dextran on a per gram basis.

Lesion Washing Study.

Figure 5A:
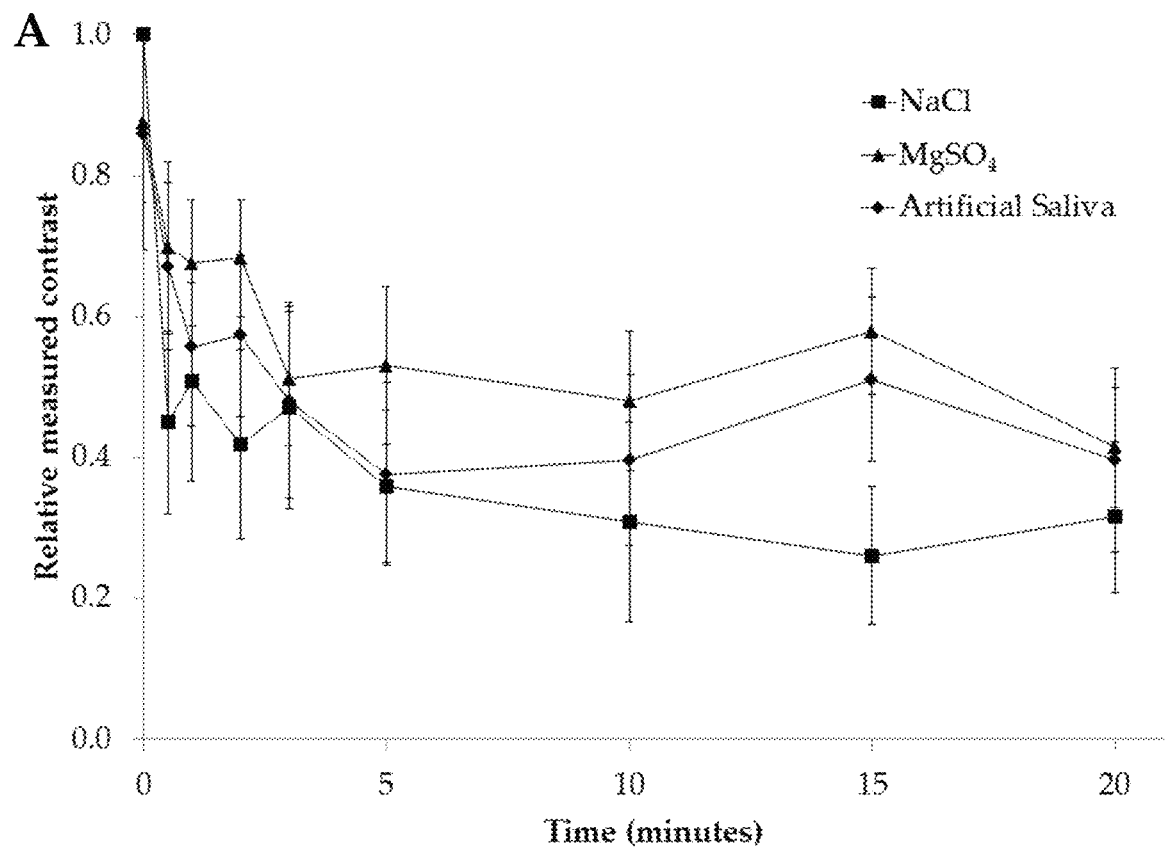
Figure 5B:
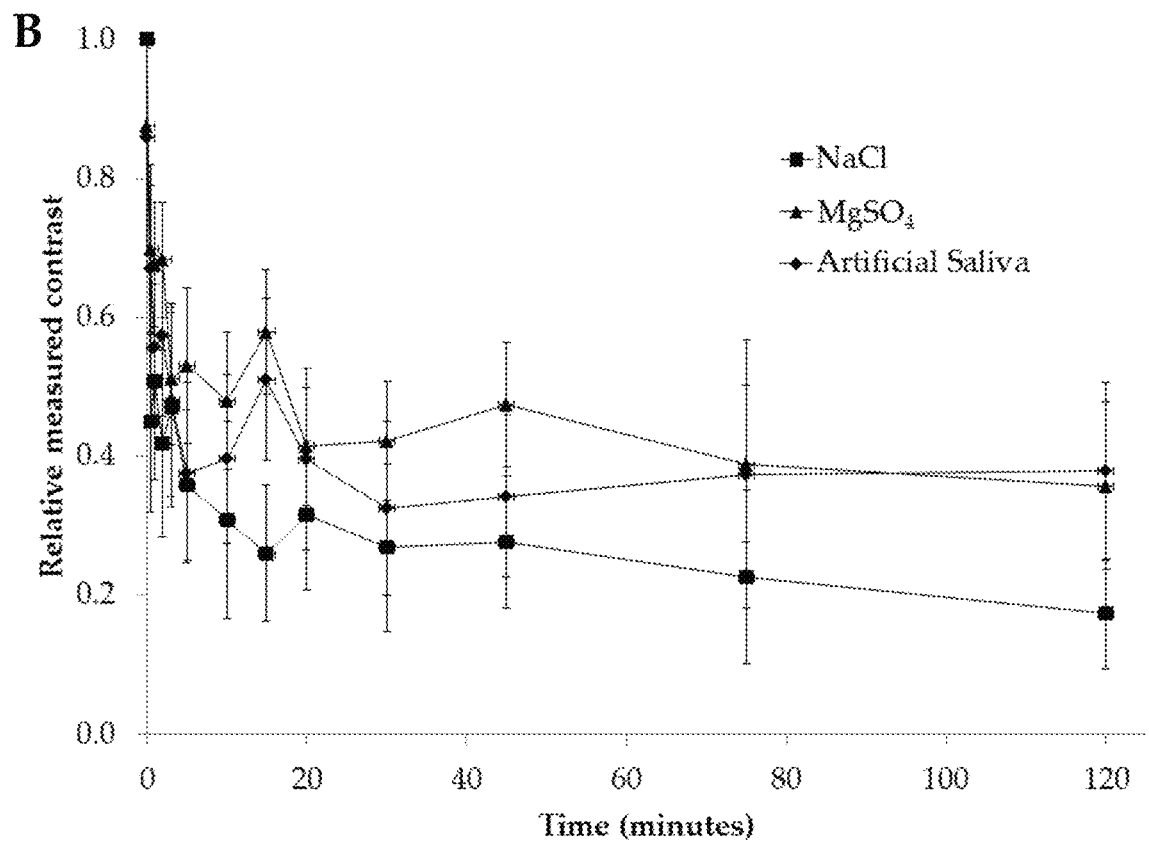

Teeth are exposed to the fluorescent cationic starch nanoparticles and imaged to provide baseline fluorescence. Three different washing conditions (1% sodium chloride solution, 1% magnesium sulfate solution, artificial saliva solution) are used to rinse the particles from the carious lesions, with images taken at intermediate time points ranging from 30 seconds to 2 hours. FIG. 5A shows fluorescence over 2 hours. FIG. 5B shows fluorescence over 20 minutes. Image analysis of the contrast is tracked to determine overall reduction in fluorescence from the lesions as a function of washing time and type of rinse fluid.

The results show that there is significant reduction in signal after the first thirty seconds as shown in FIG. 5B. There is then slow and gradual reduction in fluorescence signal over time, with approximately 65% washout in the artificial saliva and MgSO$_4$ washing solutions, and 80% washout in the NaCl washing solution after 2 hours.

Cellular Toxicity Study.

Figure 6:
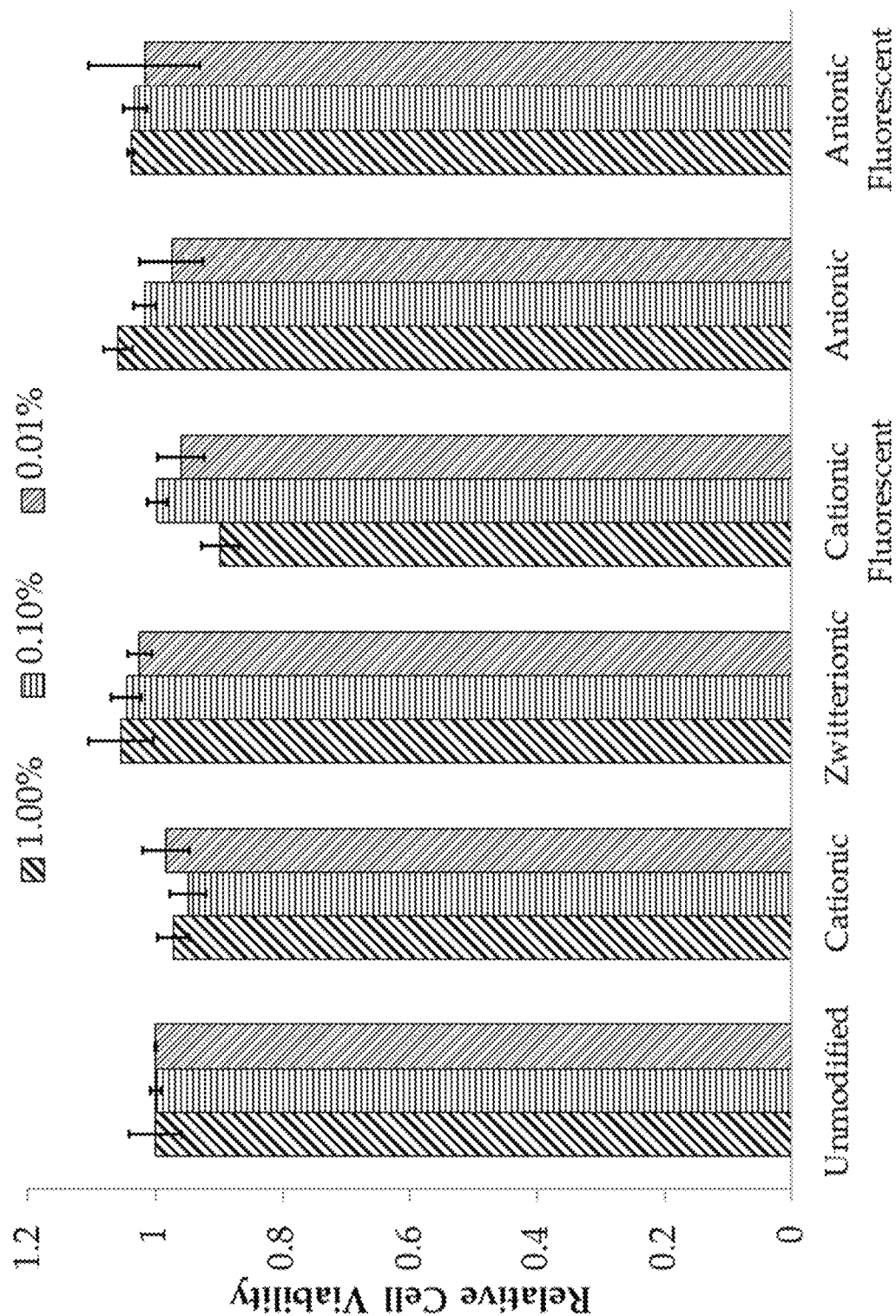

The results from a Tox8 cellular toxicity assay of modified StNPs after 2 hour exposure on HeLa cells are shown in FIG. 6. These results indicate that all the particles are nontoxic even at high concentrations of 0.01 g/ml.

Dental Activities Testing.

Figure 8:
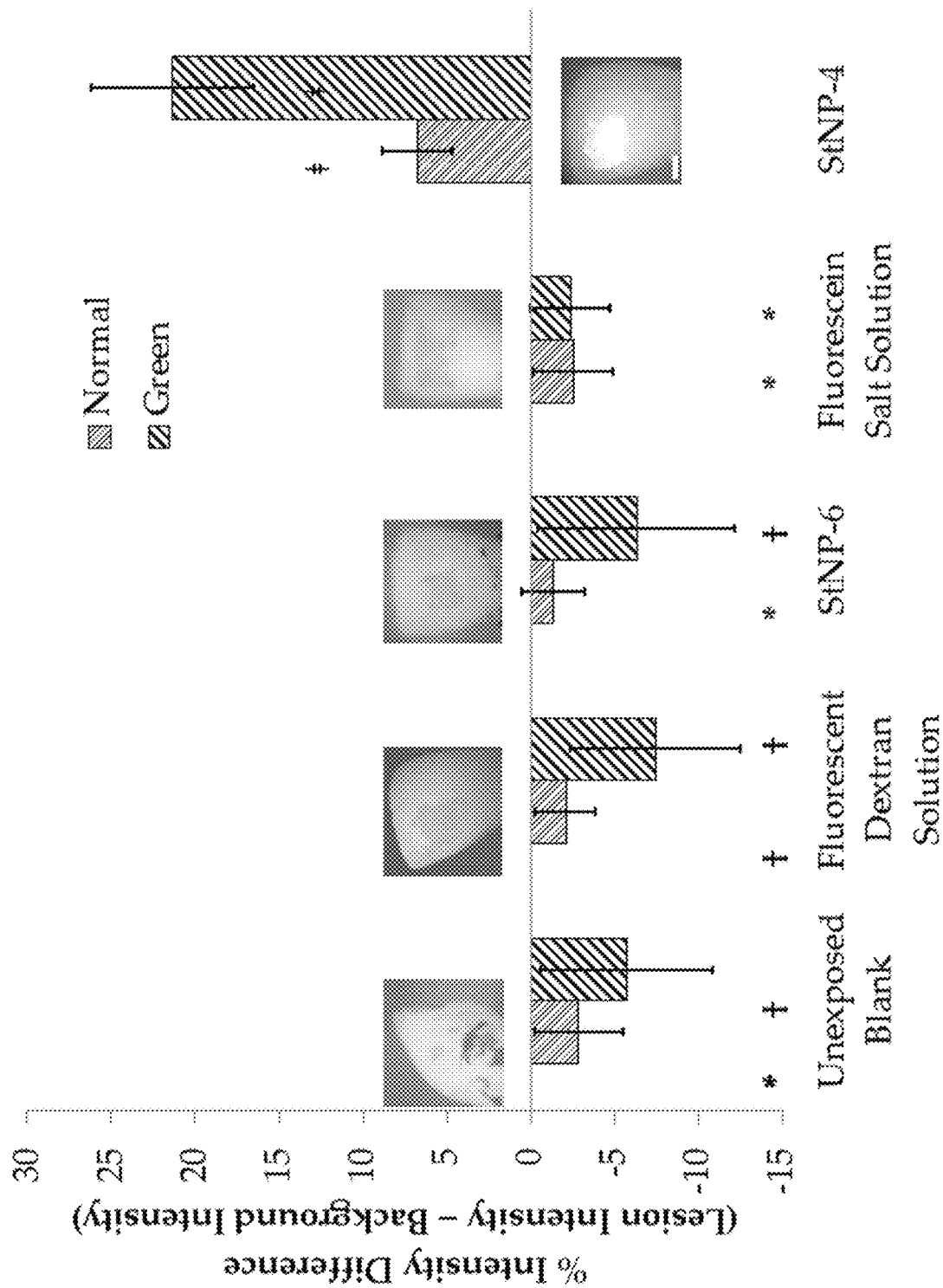
Figures 9A, 9B, 9C, 9D, 9E, 9F:
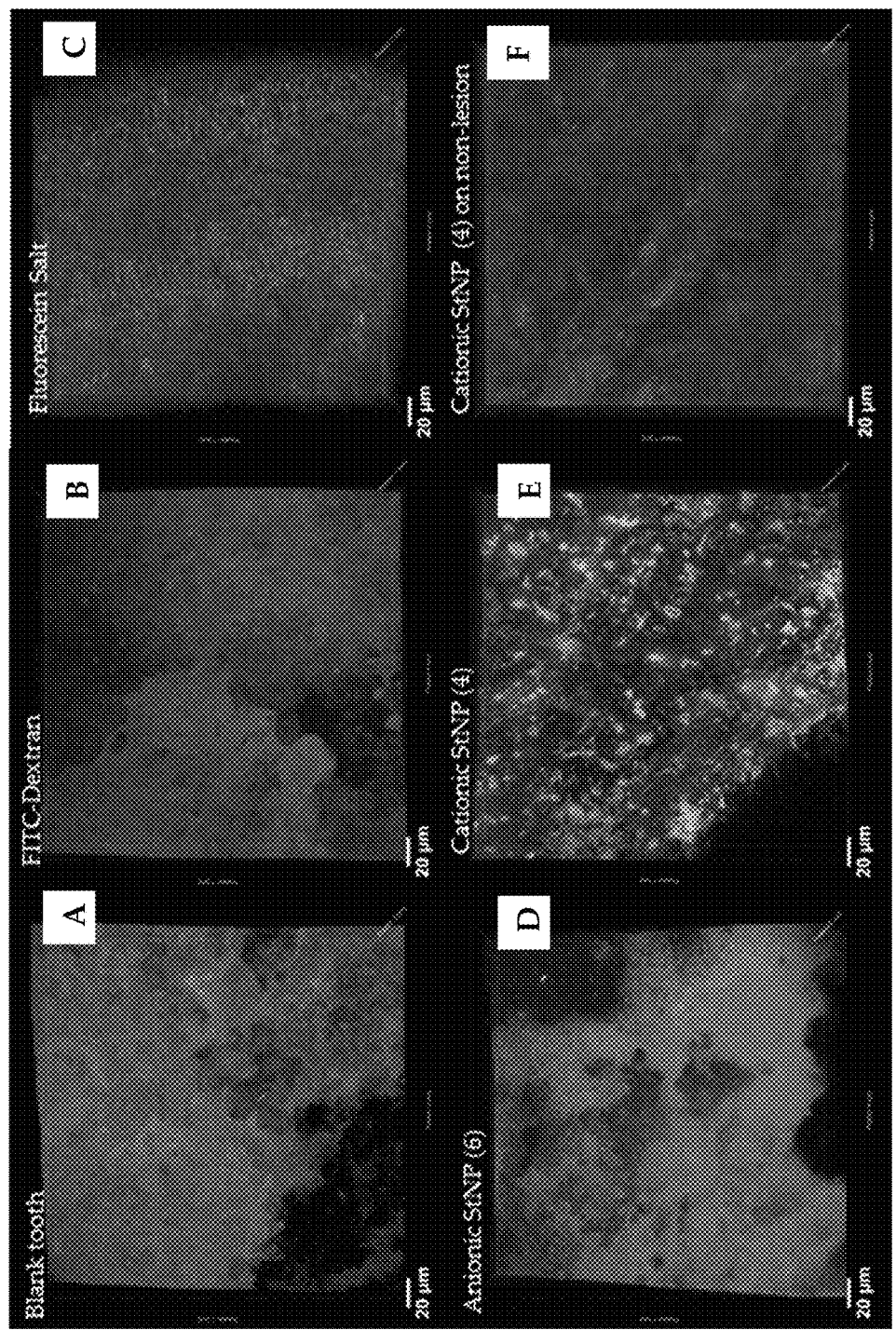

Initial testing compared fluorescein sodium salt, FITC-dextran, fluorescent anionic StNP, and fluorescent cationic StNP solutions at illuminating carious lesions. Samples are rinsed in DI water to determine a washing protocol to limit non-specific dying of the tooth. It is found that a high concentration of fluorescein sodium salt fully dyed the tooth, thus, to properly compare to the other samples, the concentration of fluorescein is reduced to $10^{-5}$ g/mL. Teeth are exposed for 3 minutes to 10 □L of $10^{-2}$ g/mL concentrations of fluorescently labeled dextran and anionic StNPs, the $10^{-5}$ g/mL solution of fluorescein sodium salt (controls), as well as a $10^{-5}$ g/mL dispersion of fluorescently labeled cationic StNPs, and then rinsed. Images are taken under a dental curing light and lesion versus background tooth intensity is compared. FIG. 8 shows % Intensity Difference for lesions minus background intensity for each, as well unexposed blank controls. "Normal" stands for % Intensity Difference obtained for normal images using ImageJ software, and "Green" stands for the extracted green pixel data from those same images. All of the controls show slight negative contrast, whereas the fluorescent cationic StNP dispersion shows 6.5% and 21% positive contrast for Normal and Green images, respectively. The exposed controls are not statistically different from blank controls, and untreated carious lesions are darker than normal background enamel of the tooth; however, fluorescein-labeled cationic StNPs significantly brightens the lesion for Normal and Green (p<$10^{-5}$) images, also improving visual contrast. Fluorescence on the teeth is clearly visible for 3 and 6.5% for Normal and Green images, respectively. Thus, the cationic StNPs selectively adsorb to active carious lesions and using fluorescein, they facilitate diagnosis. It is found that for all samples, initially the carious lesions are lit, but for rinse times of more than 20 seconds, the fluorescein, FITC-dextran and anionic StNP control groups are fully washed away. In contrast, the cationic StNP sample lit the carious lesions and rinsing for up to five minutes is unable to remove it.

Figure 7A:
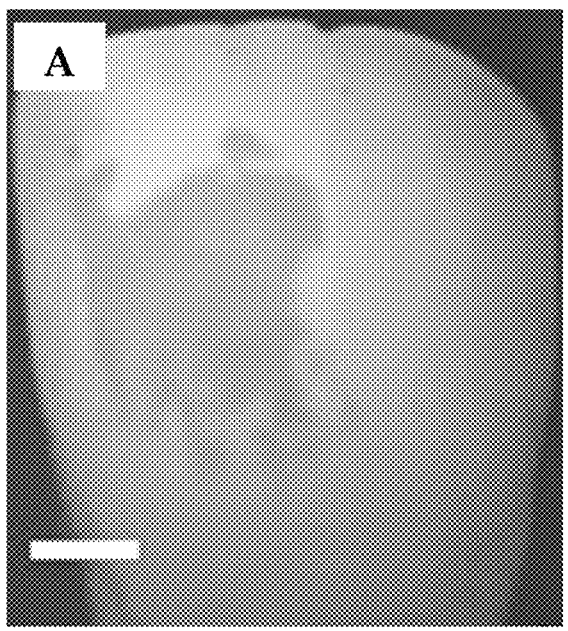
Figure 7B:
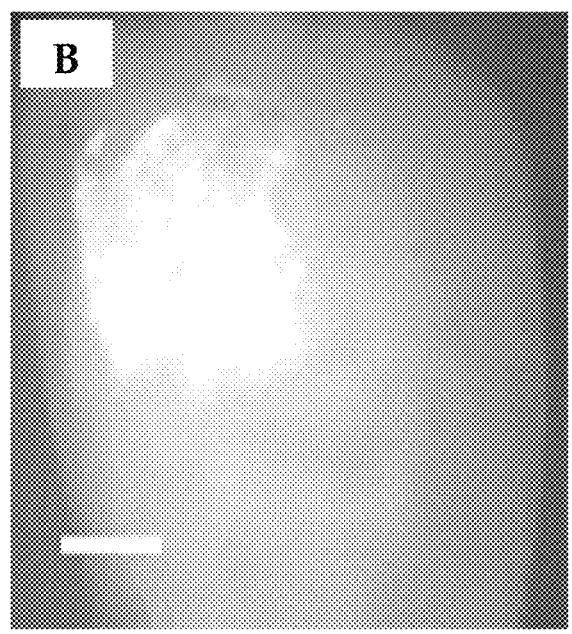

To validate the efficacy of the cationic StNPs, testing is done using first the controls, rinsing for 30 seconds, and repeating on the same tooth with cationic StNPs prepared in accordance with certain aspects of the present disclosure. Photographs are taken of the teeth as shown in FIGS. 7A-7B. There are visible changes in the color of teeth with microcavities (as shown in FIG. 7B) as compared to teeth without any microcavities (FIG. 7A) after exposure to a suspension of cationic starch nanoparticles prepared in accordance with certain aspects of the present disclosure. The photographs are modified from full-scale lighting to extract the green pixels, as this is found to significantly increase the contrast between lesion and background. The carious lesions are initially slightly darker than the rest of the tooth, and this result is consistent across all controls. The same teeth, treated with the fluorescent cationic StNPs showed fluorescence in the carious lesion region, which is visibly brighter than the background.

As mentioned above, to quantitatively analyze the images, brightness is measured using ImageJ software. The data are presented with associated pictures in FIG. 8 as a percent intensity difference comparing the carious lesion to the adjacent region of healthy tooth. Positive values indicate that the carious lesion is brighter than the background tooth, and negative values indicate that the carious lesion is darker than the background tooth. Statistical analysis confirms that untreated teeth are indistinguishable from fluorescein, fluorescent FITC-dextran, and fluorescent anionic StNP controls, meaning that these controls did not illuminate carious lesions. The analysis further suggests that untreated carious lesions are slightly distinguishable against the background tooth; however, this is not always statistically significant. In stark contrast, the teeth treated with fluorescent cationic StNPs yielded highly significant positive percent intensity differences ($p<10^{-5}$), indicating that these particles improved the contrast of carious lesions relative to the background, even to the naked eye. Additionally, analyzing extracted green-pixel images instead of standard RGD images further improved the contrast. It is interesting to note that comparing the non-illuminated images to the illuminated images highlights differences between the delineated shape of the lesion depending on the optical method used (e.g., image of carious lesions treated with fluorescent anionic particles and corresponding image of lesions treated with fluorescent cationic particles). While not being limited or bound by any particular theory, conceivably, this variation occurs because the fluorescent particles will only illuminate an active carious lesion with open porosity, while the closed pores of inactive lesions cannot be detected by the starch nanoparticles. In contrast, the non-illuminated lesion images are darker if there is sub-surface porosity. This approach by itself thus fails to identify inactive caries due to their closed surface porosity. The ability to distinguish between active and inactive lesions is a significant dental advantage of targeted nanoparticles compared to other diagnostic methods.

As a further validation of these results, images of the same teeth are taken using a fluorescence scanner with a green 542 nm bandpass filter and blue light illumination. This method is not chosen as the primary method of analysis, because of its limited translatability, though it significantly increased the contrast compared to the optical method and images obtained by camera using a dental curing light ($p<10^{-5}$). Nevertheless, these results provide further confirmation that the fluorescence seen in the carious lesions is due to the fluorescent cationic starch nanoparticles. Consequently, it can be concluded that the prepared fluorescent cationic starch nanoparticles can specifically highlight active carious lesions when illuminated with a standard dental curing lamp in vitro, and therefore offer a simple method to assist dentists in diagnosis of white spot carious lesions in vivo Although the FITC-dextran polymer solution has an average size of approximately 100 nm and a zeta potential of approximately +6 mV, and is thus mildly cationic, as a control it did not successfully associate and illuminate the carious lesions. In contrast, the cationic starch nanoparticles with a similar zeta potential did successfully associate with and illuminate the carious lesions. Without intending to be bound by theory, the cationic dextrin polymer may be held in solution by stronger forces, on an absolute basis or at least relative to the mass of the molecules in solution, as compared to the cationic starch nanoparticles. The cationic starch nanoparticles are a dispersion rather than a solution. The nanoparticle dispersion is stable, probably due to steric stabilization, yet only a mildly cationic charge is required for the nanoparticles to come out of the dispersion and associate with the carious lesions. Alternatively or additionally, the cationic starch nanoparticles may aggregate in or around an active carious lesion, perhaps aided by their zwitterionic nature, and become somewhat more resistant to rinsing, whereas a polymer in solution does not. Although a more strongly charged compound in solution might still be able to associate with a carious lesion, the lesser charge required by the nanoparticle is advantageous, in that less reactants are required to produce the mild charge and there may be a trend for toxicity with increases in cationic charge.

Two-Photon Microscopy.

Figure 10:
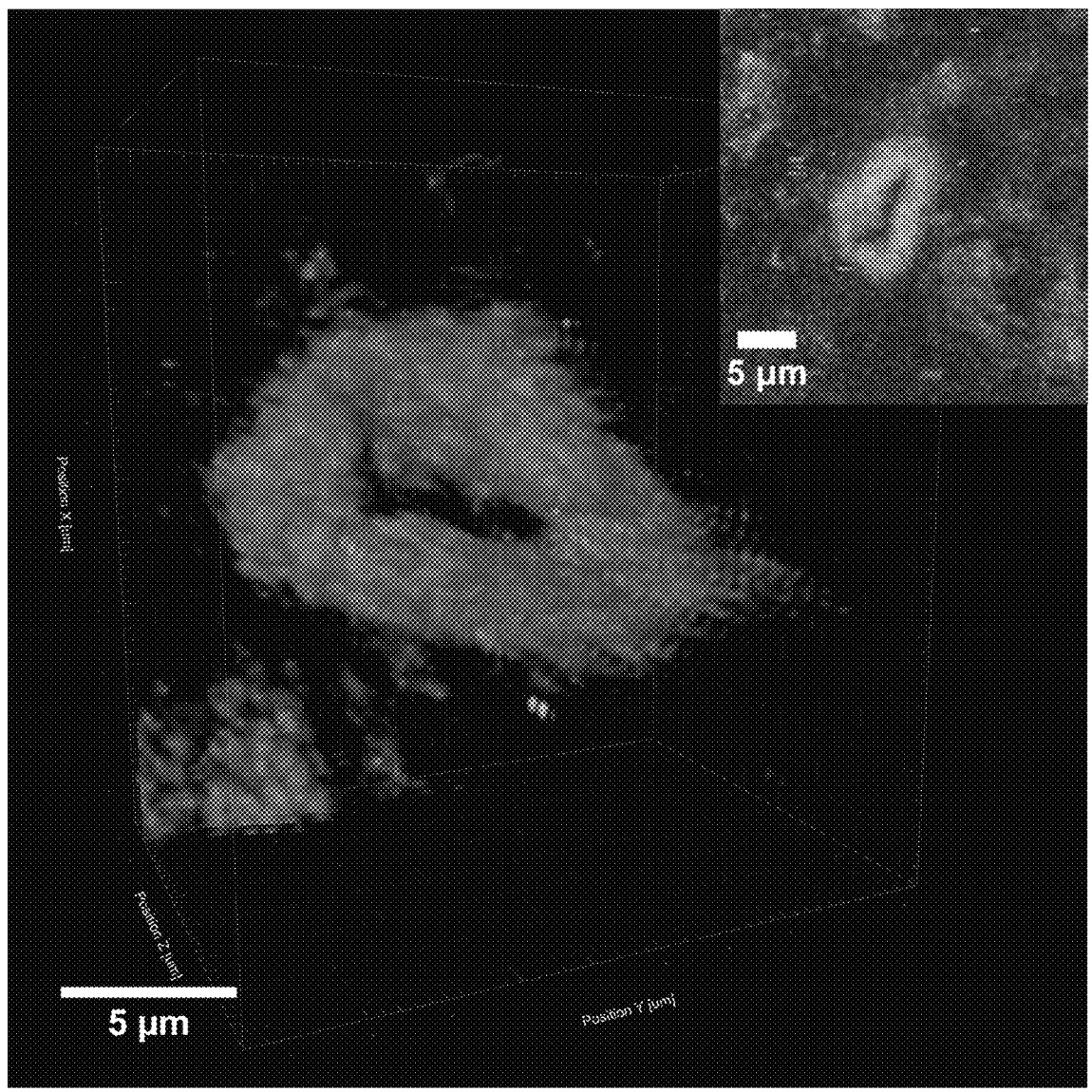

Two-Photon Microscopy images of the different conditions are shown below in FIGS. 9A-9F. It is clear that the cationic StNPs illuminate small pores in the tooth surface, which are presumably early carious lesions. Interesting ring-shaped illumination patterns such as the one shown in FIG. 10 suggest that particles are arranged on the surface of the carious lesion and do not fill the entire pore. These results suggest that Two-Photon Microscopy can be used to obtain information about the size and shape of illuminated carious lesions.

Nanoparticle Targeting to Remineralize Lesions.

Figure 13:
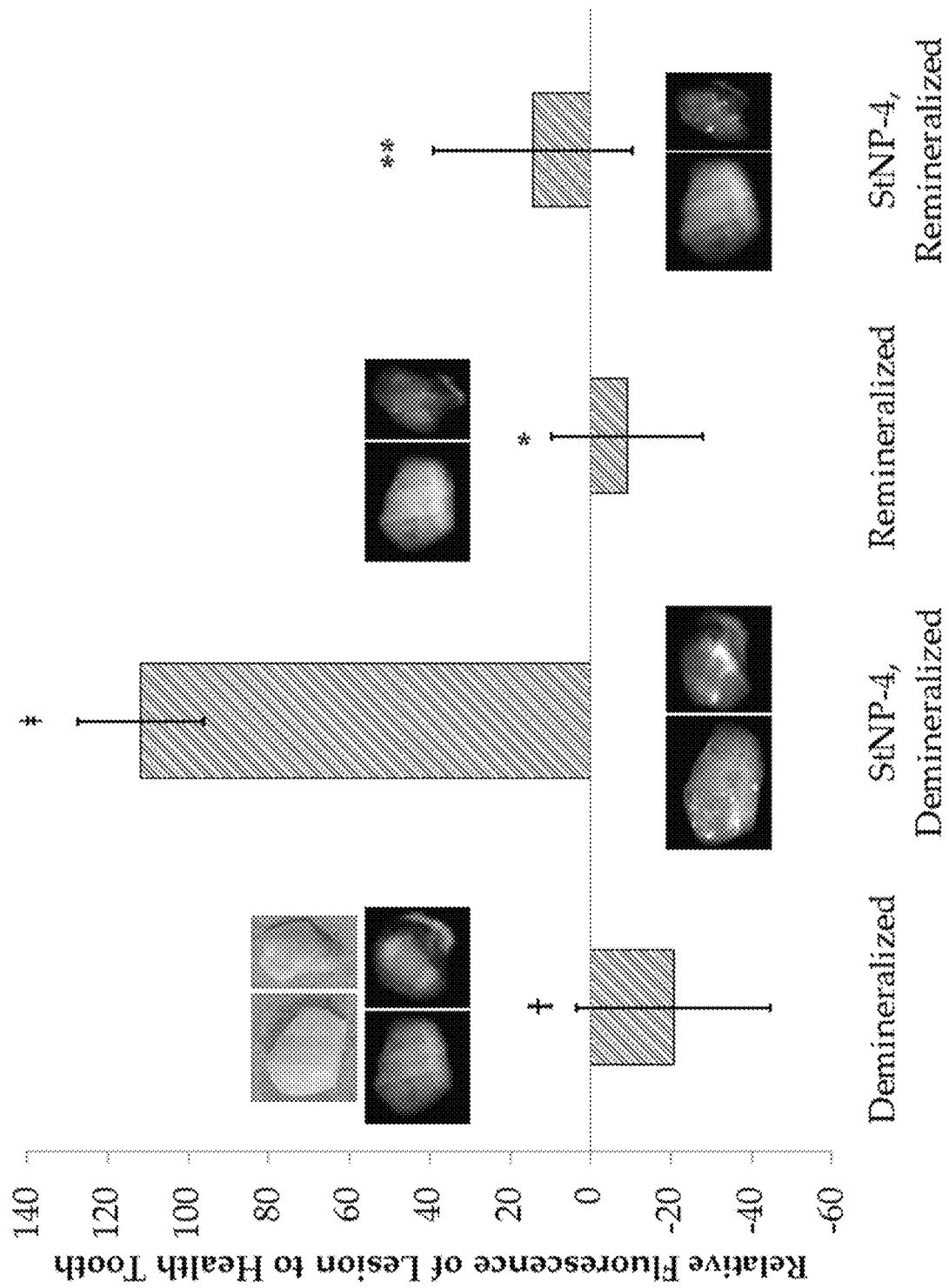
FIG. 13 shows fluorescence of demineralized and remineralized carious lesions. Remineralized (inactive) carious lesions do not illuminate after exposure to fluorescent cationic StNPs, in contrast to demineralized (active) carious lesions. *Negative contrast ($0.05<p<0.20$), †Significant negative contrast ($p<0.05$), **Positive contrast ($0.05<p<0.30$), ‡Significant positive contrast ($p<10^{-5}$).
Figure 14:
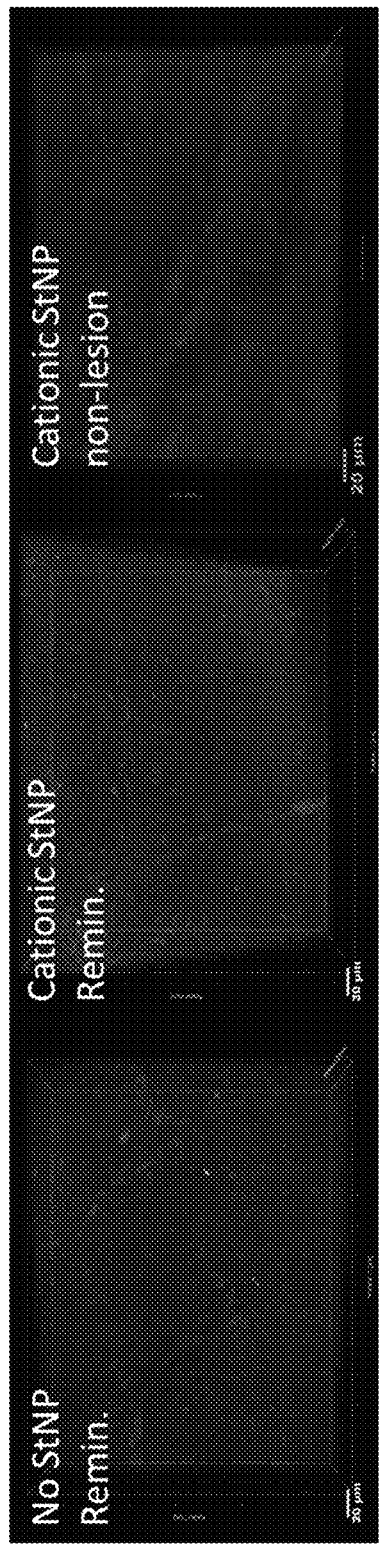
FIG. 14 shows Two-Photon micrographs of remineralized carious lesions with and without exposure to fluorescent cationic StNPs. Images most closely resemble the Two-Photon micrograph of a non-lesion surface, highlighting that remineralized lesions are "inactive" and from a surface perspective, healed.

Teeth with microcavities are remineralized using a fluoride solution to "heal" the surface porosity of the carious lesions, yielding inactive lesions with subsurface porosity. These lesions are analyzed using the same illumination and image analysis protocol before and after remineralization. The results obtained with a fluorescent scanner are shown in FIG. 13. By appearance, the remineralized (inactive) lesions are visually indistinguishable from demineralized (active) lesions (inset image in FIG. 13). Furthermore, without illumination by fluorescent cationic StNPs, the active and inactive carious lesions are indistinguishable ($p=0.44$). In contrast, after exposure to fluorescent cationic StNPs, the inactive lesions show only minimal illumination ($p=0.38$), when compared to active lesions ($p<10^{-5}$). Though a low level of fluorescence is detected for the remineralized lesions, this is most likely because the teeth are not fully remineralized during the remineralization protocol. However, in all cases, the illumination is lower for the remineralized lesions. Fundamentally, these results validate the high degree of specificity of fluorescent cationic StNPs to diagnose and differentiate between active and inactive carious lesions. Use of a specific fluorescent nanoparticle probe can identify caries activity by virtue of surface porosity, which, in active carious lesions allows for diffusion to the subsurface pores, but prevents access to the fluorescent probe in the case of inactive lesions. Clinically, a dentist does not need to treat inactive lesions, and treatments such as fluoride varnishes, gels, washes, or sealants, will have no beneficial effect. In contrast, active lesions are progressing, and appropriate treatment can halt and reverse demineralization. Two-Photon micrographs of the remineralized lesions, both before and after exposure to fluorescent cationic StNPs, further support these results (FIG. 14). These images show a smooth surface with no observable fluorescent pores, which most closely resemble a non-lesion surface after exposure to fluorescent cationic StNPs. These results highlight that the remineralized lesion, from a surface perspective, has been healed. Furthermore, dentists and clinical researchers can use the fluorescent cationic StNPs to validate and monitor effective remineralization of carious lesions after treatment, or as a compelling means of quantifying the efficacy of various treatments.

Fluoride Release Study.

A fluoride release study tests the loading of fluoride into cationic starch nanoparticles using a freeze-drying method. This is intended to be a baseline measurement as there is potential interaction of the anionic fluoride salt with the cationic starch polymer of the particles. After lyophilization, particles are immersed in a 0.01% phosphate-buffered-saline (PBS) solution, or artificial saliva (AS) solution, contained within a 100 kDa dialysis membrane. Aliquots of a half milliliter in size are taken at consecutive time points extending from 30 seconds to 72 hours. The aliquots are then tested using a fluoride electric probe to determine the fluoride concentration, and these values are normalized using a calibration to samples of known concentration. A reference solution of free fluoride salt is used as a comparison to see the diffusion-limited release of the fluoride salt through the dialysis membrane. Results of the release study are shown in FIG. 15.

The study shows that there is delay on fluoride release when lyophilized with the cationic starch nanoparticles, on the order of about 30 minutes improvement in artificial saliva (AS), or 10 minutes in phosphate buffer solution (PBS). This preliminary data suggests that the cationic starch nanoparticles can moderately bind the anionic fluoride salt to extend release, with the implication that or more swollen larger particles with various degrees of cross-linking may be desirable to further extend the release profile.

Thus, the present disclosure provides cationic nanoparticles that target and illuminate early forming active carious lesions. In certain variations, such a nanoparticle may be a starch-based fluorescent cationic nanoparticle. The particles are biodegradable and are enzymatically broken down in saliva. These particles can be illuminated using a standard dental curing lamp, comporting with current dental practices and workflow. The present technology thus improves detection of microcavities while they are still reversible and treatable by improved dental hygiene and treatment with a dental remineralizing agent, for example, fluoride and/or phosphate. Using image analysis, and in particular by analyzing the green colors in images, these particles significantly improve the contrast of carious lesions. Furthermore, Two-Photon Microscopy of teeth treated with these nanoparticles allows for analysis of the architecture of these lesions. Consequently, the nanoparticles can be used for early diagnosis of caries in dental clinics, for home use, or to monitor tooth remineralization and conservative restoration strategies in dental practices and in clinical trials and the like. Such nanoparticles can be used to deliver oral care active ingredients, such as fluoride ions, other remineralization aides, or antibacterial therapeutics to improve dental health.

In other variations, the present technology provides the ability to differentiate between inactive and active carious lesions to help monitor progression following treatment using remineralization, in order to enable dentist and dental patient to implement conservative treatment strategies, avoiding more invasive and expensive restorative procedures, such as "drill and fill" or other invasive procedures, as well as ability to reduce patient exposure to harmful radiation from taking X-Ray images, which may especially be undesirable in children.

This specification also provides diagnostic methods of one or more carious lesions, imaging methods of one or more carious legions, methods of caries treatment, methods of remineralization, methods of monitoring caries treatment, uses of a component (e.g., compound) or a nanoparticle as described above as a medicament, or uses of a component (e.g., compound) or nanoparticle as a diagnostic agent.

The present disclosure also describes a fluorescent, optionally starch-based, component (e.g., compound) or nanoparticle having a net positive charge, and the use of such component (e.g., compound) or nanoparticles to aid in the diagnosis, imaging and/or monitoring of caries.

The present disclosure also describes an optionally starch-based component or nanoparticle comprising a re-mineralizing agent, wherein the nanoparticle has a net positive charge, and such components or nanoparticles used in the treatment of caries.

In yet other aspects, the present disclosure contemplates use of a positively-charged fluorescent composition to determine a location of caries on teeth.

In still further aspects, the present disclosure contemplates use of a positively-charged comprising a component or nanoparticle comprising a re-mineralizing agent in a medicament for treatment of caries.

All possible combinations discussed and enumerated above and herein as optional features of the inventive materials and inventive methods of the present disclosure are specifically disclosed as embodiments. In various aspects, the present disclosure contemplates a composition for oral administration comprising a component that comprises a biocompatible polymer and an imaging agent, an oral care active ingredient, or both the imaging agent and the active ingredient. The composition has a cationic moiety or a net positive charge. Also specifically disclosed are the combinations including this composition with any one or any combination of more than one of the enumerated features (1)-(23) below.

For example, the composition optionally has any one or any combination of more than one of the following features: (1) the cationic moiety is bonded with the biocompatible polymer; (2) the biocompatible polymer comprises a tertiary amine or a quaternary amine; (3) the biocompatible polymer comprises a reaction product of glycidyl trimethyl ammonium chloride bonded to the biocompatible and biodegradable polymer; (4) the biocompatible polymer is selected from the group consisting of: a mono-, oligo- or polysaccharide, carboxymethylcellulose, polymeric starch, dextrin, dextran, chitosan, cellulose, gelatin, polyethyleneimine (PEI), poly(L-lysine) (PLL), poly(L-arginine), poly(amidoamine) (PAA), poly (amino-co-ester) (PAE), poly(2-N,N-dimethylaminoethylmethacrylate) PDMAEMA, poly(4-vinylpyridine) (P4VP), polyester, poly(acrylic acid), poly (methacrylic acid), a polyalkylene glycol, a methyl vinyl ether/maleic anhydride copolymer, and combinations thereof; (5) the biocompatible polymer is a cationic polymer selected from the group consisting of: a cationic or cationically modified mono-, oligo- or polysaccharide, carboxymethylcellulose, starch, dextrin, dextran, chitosan, cellulose, gelatin, polyethyleneimine (PEI), poly(L-lysine) (PLL), poly(L-arginine), poly(amidoamine) (PAA), poly (amino-co-ester) (PAE), poly(2-N,N-dimethylaminoethylmethacrylate) PDMAEMA, poly(4-vinylpyridine) (P4VP), and combinations thereof; (6) the imaging agent comprises a fluorophore that fluoresces in response to electromagnetic radiation from a dental curing lamp; (7) the imaging agent comprises at least one biocompatible dye; (8) the imaging agent is capable of detection by visual inspection or digital photography of the oral cavity while exposing the imaging agent to electromagnetic radiation from a dental curing lamp; (9) the visual inspection or digital photography comprises use of an optical filter or filtering of the digital image; (10) the composition has the net positive charge and/or a zeta potential of greater than or equal to about +2 mV at a pH of 7; (11) the biocompatible polymer is zwitterionic; (12) the component is a nanoparticle having an average particle size of greater than or equal to about 10 nm to less than or equal to about 500 nanometers; (13) the oral care active ingredient is selected from the group consisting of: an anti-caries agent, a remineralizing agent, an anti-bacterial agent, an anti-calculus agent, and combinations thereof; (14) the anti-caries agent is selected from the group consisting of: a fluoride-containing agent, a remineralizing agent, and combinations thereof; (15) the oral care active ingredient comprises a fluoride-containing component present at greater than or equal to about 0.02% to less than or equal to about 2.2% by weight after incorporation into the component, wherein the fluoride-containing component is selected from the group consisting of: fluorohydroxyapatite, stannous fluoride, sodium fluoride, calcium fluoride, silver fluoride dehydrate, sodium monofluorophosphate, difluorosilane, and combinations thereof; (16) the oral care active ingredient comprises a calcium-containing component present at greater than or equal to about 1% to less than or equal to about 5% by weight after incorporation into the component; (17) the oral care active ingredient is an anti-caries agent comprising a calcium and phosphate-containing component, wherein the calcium and phosphate-containing component comprises:
  (a) calcium glycerophosphate present in the composition at greater than or equal to about 0.1% to less than or equal to about 1% by weight after incorporation into the composition;
  (b) dicalcium phosphate present in the composition at greater than or equal to about 2% to less than or equal to about 50% by weight after incorporation into the composition;
  (c) tricalcium phosphate present in the composition at greater than or equal to about 1% to less than or equal to about 5% by weight after incorporation into the composition; or
  (d) calcium sodium phosphosilicate present in the composition at greater than or equal to about 1% to less than or equal to about 10% by weight after incorporation into the composition;
(18) wherein the oral care active ingredient is selected from the group consisting of:
  (a) amine fluoride present in the composition at greater than or equal to about 0.2% to less than or equal to about 2.2% by weight after incorporation into the composition;
  (b) casein phosphopeptide present in the nanoparticle at greater than or equal to about 1% to less than or equal to about 5% by weight after incorporation into the composition; and
  (c) phosphoprotein present in the composition at greater than or equal to about 0.001% to less than or equal to about 0.01% by weight after incorporation into the composition;
(19) the composition has a degradation time of greater than or equal to about 30 minutes to less than or equal to about 30 days after introduction into the oral cavity; (20) the component is a nanoparticle comprising multiple distinct compartments; (21) the composition further comprises an orally acceptable carrier; (22) the orally acceptable carrier is selected from the group consisting of: a mouth rinse, a paint, a gel, and a dentifrice; and/or (23) the component is a nanoparticle and the composition comprises a first plurality of diagnostic nanoparticles and a second plurality of therapeutic nanoparticles comprising the oral care active ingredient.

In other aspects, the present disclosure contemplates a nanoparticle for oral administration comprising a biocompatible and biodegradable polymer bearing at least one cationic region capable of associating with one or more carious lesions on a tooth in an oral cavity of a subject; and an imaging agent bonded to the biocompatible and biodegradable polymer, so that the nanoparticle is capable of indicating the presence of one or more carious lesions when the nanoparticle is associated therewith. Also specifically disclosed are the combinations including this composition with any one or any combination of more than one of the enumerated features (24)-(43) below.

The nanoparticle of this embodiment optionally has any one or any combination of more than one of the following features: (24) the at least one cationic region comprises a cationic moiety bonded with the biocompatible and biodegradable polymer; (25) the cationic moiety comprises a tertiary amine or a quaternary amine; (26) the cationic moiety is a reaction product of glycidyl trimethyl ammonium chloride bonded to the biocompatible and biodegradable polymer; (27) the biocompatible and biodegradable polymer is a cationic polymer selected from the group consisting of: a cationic or cationically modified mono-, oligo-, or polysaccharide, carboxymethylcellulose, starch, dextrin, dextran, chitosan, cellulose, gelatin, polyethyleneimine (PEI), poly(L-lysine) (PLL), poly(L-arginine), poly (amidoamine) (PAA), poly (amino-co-ester) (PAE), poly(2-N,N-dimethylaminoethylmethacrylate) PDMAEMA, poly (4-vinylpyridine) (P4VP), and combinations thereof; (28) the imaging agent comprises a fluorophore that fluoresces in response to electromagnetic radiation from a dental curing lamp; (29) the imaging agent comprises at least one biocompatible dye; (30) the imaging agent is capable of detection by visual inspection of the oral cavity; (31) the visual inspection comprises use of an optical filter; (32) the nanoparticle has a zeta potential of greater than or equal to about 0 mV to less than or equal to about +50 mV at a pH of 7; (33) the nanoparticle is zwitterionic; (34) the nanoparticle has an average diameter of greater than or equal to about 10 nm to less than or equal to about 1,000 nanometers; (35) the biocompatible and biodegradable polymer is a polymer selected from the group consisting of: a mono-, oligo-, or polysaccharide, carboxymethylcellulose, polymeric starch, dextrin, dextran, chitosan, cellulose, gelatin, polyethyleneimine (PEI), poly(L-lysine) (PLL), poly(L-arginine), poly (amidoamine) (PAA), poly (amino-co-ester) (PAE), poly(2-N,N-dimethylaminoethylmethacrylate) PDMAEMA, poly (4-vinylpyridine) (P4VP), polyesters, poly(acrylic acid), poly(methacrylic acid), a polyalkylene glycol, a methyl vinyl ether/maleic anhydride copolymer, and combinations thereof; (36) further comprising an oral care active ingredient; (37) the oral care active ingredient comprises an anti-caries agent, a remineralizing agent, an antibacterial agent, an anticalculus agent, and combinations thereof; (38) the oral care active ingredient comprises a fluoride-containing component present at greater than or equal to about 0.02% to less than or equal to about 2.2% by weight after incorporation into the nanoparticle, wherein the fluoride-containing component is selected from the group consisting of: fluorohydroxyapatite, stannous fluoride, sodium fluoride, calcium fluoride, silver fluoride dehydrate, sodium monofluorophosphate, difluorosilane, and combinations thereof; (39) the oral care active ingredient comprises a calcium-containing component present at greater than or equal to about 1% to less than or equal to about 5% by weight after incorporation into the nanoparticle; (40) the oral care active ingredient comprises a calcium and phosphate-containing component, wherein the calcium and phosphate-containing component comprises:
  (a) calcium glycerophosphate present in the nanoparticle at greater than or equal to about 0.1% to less than or equal to about 1% by weight after incorporation into the nanoparticle;
  (b) dicalcium phosphate present in the nanoparticle at greater than or equal to about 2% to less than or equal to about 50% by weight after incorporation into the nanoparticle;
  (c) tricalcium phosphate present in the nanoparticle at greater than or equal to about 1% to less than or equal to about 5% by weight after incorporation into the nanoparticle; or
  (d) calcium sodium phosphosilicate present in the nanoparticle at greater than or equal to about 1% to less than or equal to about 10% by weight after incorporation into the nanoparticle;
(41) the oral care active ingredient comprises:
  (a) amine fluoride present in the nanoparticle at greater than or equal to about 0.2% to less than or equal to about 2.2% by weight after incorporation into the nanoparticle;
  (b) casein phosphopeptide present in the nanoparticle at greater than or equal to about 1% to less than or equal to about 5% by weight after incorporation into the nanoparticle; and
  (c) phosphoprotein present in the nanoparticle at greater than or equal to about 0.001% to less than or equal to about 0.01% by weight after incorporation into the nanoparticle;
(42) the nanoparticle degrades in a time period of greater than or equal to about 30 minutes to less than or equal to about 30 days after introduction into the oral cavity; and/or (43) comprising multiple distinct compartments.

In other aspects, the present disclosure contemplates an oral care composition for oral administration in an oral cavity of a subject comprising a plurality of nanoparticles, wherein each nanoparticle comprises a biocompatible and biodegradable polymer bearing at least one cationic region having a positive charge capable of associating with one or more carious lesions on a tooth in the oral cavity of the subject; and an imaging agent bonded to the biocompatible and biodegradable polymer, so that the plurality of nanoparticles is capable of indicating the presence of one or more carious lesions when the nanoparticles are associated therewith; and an orally acceptable carrier. Also specifically disclosed are the combinations including this composition with any one or any combination of more than one of the enumerated features (44)-(46) below.

The oral care composition of this embodiment optionally has any one or any combination of more than one of the following features: (44) the oral care composition is selected from the group consisting of: mouth rinse, paint, gel, and dentifrice; (45) the plurality of nanoparticles selectively accumulate within cavities in the tooth corresponding to the one or more carious lesions; and/or (46) the plurality of nanoparticles is a first plurality of diagnostic nanoparticles and the oral care composition further comprises a second plurality of therapeutic nanoparticles comprising an oral care active ingredient.

In yet other aspects, the present disclosure contemplates a method of making a nanoparticle for oral administration comprising functionalizing a biocompatible and biodegradable polymer with a reactive group capable of reacting with an imaging agent, wherein the biocompatible and biodegradable polymer comprises at least one cationic region capable of associating with one or more carious lesions on a tooth in an oral cavity of a subject. The method also includes reacting the reactive group on the biocompatible and biodegradable polymer with the imaging agent, so that the nanoparticle bears the imaging agent that is capable of indicating the presence of one or more carious lesions when the nanoparticle is associated therewith.

Also specifically disclosed are combinations including this method optionally with any one or any combination of more than one of the enumerated steps or features (47)-(48). The method of making a nanoparticle for oral administration optionally has any one or any combination of more than one of the following steps or features: (47) further comprising reacting the biocompatible and biodegradable polymer with a cationic moiety before the functionalizing to form the at least one cationic region; and/or (48) further comprising functionalizing the biocompatible and biodegradable polymer to have at least one first reactive group capable of reacting with the cationic moiety before the reacting with the cationic moiety.

In yet other aspects, the present disclosure contemplates a method of making a composition for oral administration comprising functionalizing a polymer with a reactive group capable of reacting with an imaging agent, wherein the polymer comprises at least one cationic region. The method also comprises reacting the reactive group on the polymer with the imaging agent, wherein the composition has a net positive charge.

Also specifically disclosed are combinations including this method optionally with any one or any combination of more than one of the enumerated steps or features (49)-(52). The method of making a composition for oral administration optionally has any one or any combination of more than one of the following steps or features: (49) further comprising reacting the polymer with a cationic moiety before the functionalizing to form the at least one cationic region; (50) further comprising functionalizing the polymer to have at least one first reactive group capable of reacting with the cationic moiety before the reacting with the cationic moiety; (51) wherein the polymer comprises hydroxy groups; and/or (52) wherein the polymer comprises glucose repeat units.

In yet other aspects, the present disclosure contemplates a method of detecting caries comprising introducing a positively-charged fluorescent component to an oral cavity of a subject. Light is directed into the oral cavity. The method further includes identifying a location of any fluorescence in the oral cavity, which may correspond to a location of one or more caries in the oral cavity.

Also specifically disclosed are combinations including this method optionally with any one or any combination of more than one of the enumerated steps or features (53)-(59). The method of detecting caries optionally has any one or any combination of more than one of the following steps or features: (53) the light is generated by a dental curing lamp; (54) further comprising rinsing the oral cavity after introducing the positively-charged fluorescent component and before the directing of the light into the oral cavity; (55) further comprising producing a digital image of the fluorescence; (56) further comprising filtering the digital image; (57) further comprising treating to the location with a remineralizing agent; (58) where the treating is repeated in multiple steps; and/or (59) further comprising subsequently repeating the introducing, the directing, and the identifying to determine if the fluorescence has increased, decreased, or remained unchanged.

In a further aspect, the present disclosure contemplates a method of treating caries comprising introducing a positively-charged nanoparticle comprising a remineralizing agent to an oral cavity of a subject. The positively-charged nanoparticle is capable of associating with one or more carious lesions in the oral cavity of the subject.

In a still further aspect, the present disclosure contemplates use of a positively-charged fluorescent composition according to any of the variations previously described above to determine a location of caries on at least one tooth in a subject.

In another aspect, the present disclosure contemplates use of a positively-charged component or nanoparticle comprising a re-mineralizing agent in a medicament for treatment of caries. The positively-charged component or nanoparticle may be any of the variations previously described above.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A nanoparticle for administration in an oral cavity of a subject comprising:
    a plurality of molecules of a starch polymer aggregated and/or crosslinked together to form the nanoparticle, the starch polymer bearing at least one cationic region for associating the nanoparticle with a subsurface portion of one or more carious lesions in a tooth in an oral cavity of a subject; and,
    an oral care active ingredient selected from the group consisting of: an anticaries agent, a remineralizing agent, and combinations thereof.

2. The nanoparticle of claim 1, wherein the oral care active ingredient comprises a fluoride-containing component, a calcium-containing component, and/or a calcium and phosphate-containing component.

3. The nanoparticle of claim 1 wherein the oral care active ingredient is present at greater than or equal to about 0.1% to less than or equal to about 50% by weight of the nanoparticle.

4. The nanoparticle of claim 1, wherein the oral care active ingredient comprises a calcium-containing component.

5. The nanoparticle of claim 4, wherein the calcium-containing component is present at greater than or equal to about 1% to less than or equal to about 5% by weight after incorporation into the nanoparticle.

6. The nanoparticle of claim 1, wherein the oral care active ingredient comprises a calcium and phosphate-containing component.

7. The nanoparticle of claim 6, wherein the calcium and phosphate-containing compound comprises one or more of:
    a) calcium glycerophosphate;
    b) dicalcium phosphate;
    c) tricalcium phosphate; and,
    d) calcium sodium phosphosilicate.

8. The nanoparticle of claim 1, wherein the oral care active ingredient comprises a fluoride-containing component.

9. The nanoparticle of claim 8 wherein the fluoride-containing component comprises calcium fluoride.

10. The nanoparticle of claim 1 wherein the oral care active ingredient comprises one or more of:
    a) amine fluoride;
    b) casein phosphopeptide; and,
    c) phosphoprotein.

11. The nanoparticle of claim 1, wherein the at least one cationic region comprises a cationic moiety bonded with the starch polymer.

12. The nanoparticle of claim 11, wherein the cationic moiety comprises a tertiary amine, a quaternary amine, or a reaction product of glycidyl trimethyl ammonium chloride.

13. The nanoparticle of claim 1, wherein the nanoparticle has a zeta potential of greater than +2 mV to less than or equal to about +30 mV at a pH of 7.

14. The nanoparticle of claim 1, wherein the nanoparticle is zwitterionic.

15. The nanoparticle of claim 1, wherein the nanoparticle has an average diameter of greater than or equal to about 10 nm to less than or equal to about 500 nm.

16. The nanoparticle of claim 1, wherein the plurality of molecules of the starch polymer is crosslinked.

17. The nanoparticle of claim 1 that is adapted to selectively accumulate within the subsurface portion.

18. An oral care composition for administration in an oral cavity of a subject comprising:
    a plurality of nanoparticles each comprising:
        a plurality of molecules of a starch polymer aggregated and/or crosslinked together to form each of the plurality of nanoparticles, the starch polymer bearing at least one cationic region for associating the nanoparticle with a subsurface portion of one or more carious lesions in a tooth in the oral cavity of the subject; and,
        an oral care active ingredient selected from the group consisting of: an anticaries agent, a remineralizing agent, and combinations thereof; and,
    an orally acceptable carrier comprising water, wherein the plurality of nanoparticles form a dispersion in the orally acceptable carrier.

19. The oral care composition of claim 18, wherein the oral care composition is selected from the group consisting of: a mouth rinse and a gel.

* * * * *